United States Patent
Williamson et al.

(10) Patent No.: US 10,359,618 B2
(45) Date of Patent: Jul. 23, 2019

(54) MULTISPECTRAL STEREOSCOPIC ENDOSCOPE SYSTEM AND USE OF SAME

(71) Applicant: Nikon Corporation, Tokyo (JP)

(72) Inventors: David M. Williamson, Tucson, AZ (US); Brian L. Stamper, Tucson, AZ (US)

(73) Assignee: NIKON CORPORATION, Tokyo (JP)

( * ) Notice: Subject to any disclaimer, the term of this patent is extended or adjusted under 35 U.S.C. 154(b) by 109 days.

(21) Appl. No.: 15/393,705

(22) Filed: Dec. 29, 2016

(65) Prior Publication Data

US 2017/0199371 A1    Jul. 13, 2017

Related U.S. Application Data

(60) Provisional application No. 62/376,279, filed on Aug. 17, 2016, provisional application No. 62/277,328, filed on Jan. 11, 2016.

(51) Int. Cl.
*A61B 1/00* (2006.01)
*A61B 1/04* (2006.01)
(Continued)

(52) U.S. Cl.
CPC ........ *G02B 23/243* (2013.01); *A61B 1/00193* (2013.01); *A61B 1/04* (2013.01);
(Continued)

(58) Field of Classification Search
None
See application file for complete search history.

(56) References Cited

U.S. PATENT DOCUMENTS 4,123,144 A * 10/1978 Mandler ................. G02B 9/42
                                                    359/777
4,751,571 A    6/1988 Lillquist
(Continued)

FOREIGN PATENT DOCUMENTS

WO          9633436 A1    10/1996
WO       2014083489 A1     6/2014

OTHER PUBLICATIONS

Cohen M, Chemla F, Buey T, Gendron É, Hubert Z, Hartl M, Clénet Y, Davies R. Optical design of the relay optics for the micado scao system. InAdaptive Optics Systems IV Aug. 7, 2014 (vol. 9148, p. 914833). International Society for Optics and Photonics. (Year: 2014).*

(Continued)

*Primary Examiner* — Clifford Hilaire
(74) *Attorney, Agent, or Firm* — Yakov S. Sidorin; Quarles & Brady LLP

(57) ABSTRACT

Optical objective dimensioned to operate as part of intravascular endoscope probe and including first and second groups of lens elements. The first group of lens elements includes a first meniscus lens with a negative dioptric power and a first optical doublet. The second group of lens elements include a sequence of second, third, and fourth optical doublets and a second meniscus lens with a positive dioptric power. At least one of the first and second groups of lens elements includes an aspheric refractive surface, thereby reducing distortion down to under 1% for field angles up to at least 40 degrees. Methods for using same, including embodiments with such multiple optical objectives used for acquisition of images of targets with fixed FOV and image fusion, providing enhanced imaging data for target analysis.

24 Claims, 16 Drawing Sheets

(51) Int. Cl.
| | |
|---|---|
| *G02B 13/22* | (2006.01) |
| *G02B 23/24* | (2006.01) |
| *G02B 9/62* | (2006.01) |
| *H04N 5/33* | (2006.01) |
| *H04N 13/156* | (2018.01) |
| *H04N 13/204* | (2018.01) |
| *H04N 13/239* | (2018.01) |
| *H04N 5/225* | (2006.01) |

(52) U.S. Cl.
CPC ............... *G02B 9/62* (2013.01); *G02B 13/22* (2013.01); *G02B 23/2415* (2013.01); *H04N 5/332* (2013.01); *H04N 13/156* (2018.05); *H04N 13/204* (2018.05); *H04N 13/239* (2018.05); *H04N 2005/2255* (2013.01)

(56) References Cited

U.S. PATENT DOCUMENTS

| | | | |
|---|---|---|---|
| 5,311,018 A | 5/1994 | Zana et al. | |
| 5,555,324 A | 9/1996 | Waxman et al. | |
| 5,910,816 A | 6/1999 | Fontenot et al. | |
| 6,618,207 B2 | 9/2003 | Lei | |
| 6,652,452 B1 | 11/2003 | Seifert et al. | |
| 6,994,668 B2 | 2/2006 | Miyano | |
| 7,053,928 B1 | 5/2006 | Connors et al. | |
| 7,274,830 B2 | 9/2007 | Bacarella et al. | |
| 7,821,720 B2 | 10/2010 | Wang et al. | |
| 8,824,833 B2 | 9/2014 | Dagher et al. | |
| 2004/0156120 A1* | 8/2004 | Yoneyama | G02B 15/177 359/680 |
| 2008/0024608 A1 | 1/2008 | Hahn et al. | |
| 2008/0252997 A1 | 10/2008 | Duckett | |
| 2009/0015938 A1* | 1/2009 | Harada | G02B 13/06 359/676 |
| 2009/0052064 A1* | 2/2009 | Caldwell | G02B 13/18 359/793 |
| 2009/0096865 A1* | 4/2009 | McKinley | G02B 23/2415 348/45 |
| 2009/0195866 A1* | 8/2009 | Kawaski | G01N 21/6458 359/385 |
| 2009/0303317 A1 | 12/2009 | Tesar | |
| 2011/0002051 A1 | 1/2011 | Hsu et al. | |
| 2011/0002052 A1 | 1/2011 | Nasu | |
| 2011/0249014 A1 | 10/2011 | Kolstad et al. | |
| 2011/0249323 A1 | 10/2011 | Tesar et al. | |
| 2013/0057666 A1 | 3/2013 | Fujii | |
| 2014/0104563 A1* | 4/2014 | Bakaraju | G02C 7/061 351/159.41 |
| 2014/0169658 A1 | 6/2014 | Kowalevicz | |

OTHER PUBLICATIONS

Kopon D, Close LM, Males JR, Gasho V. Design, implementation, and on-sky performance of an advanced apochromatic triplet atmospheric dispersion corrector for the Magellan adaptive optics system and VisAO camera. Publications of the Astronomical Society of the Pacific. Jul. 23, 2013;125(930):966. (Year: 2013).*

Adu, et al., Multi-Focus Image Fusion Based on WNMF and Focal Point Analysis, Journal of Convergence Information Technology, 2011, 6(7):109-117.

Geng, et al., Multi-Focus Image Fusion Using the Local Neighbor Sum of Laplacian in NSCT Domain, International Journal of Signal Processing, Image Processing and Pattern Recognition, 2013, 6(4):69-80.

Hariharan, et al., Multifocus Image Fusion by Establishing Focal Connectivity, In 2007 IEEE International—Conference on Image Processing, 2007, 3:III-321 thru III-324.

James, et al., Medical Image Fusion: A Survey of the State of the Art, Information Fusion, 2014, 19:4-19.

Pelapur, et al., Multi-Focus Image Fusion Using Epifluorescence Microscopy for Robust Vascular Segmentation, In 2014 36th Annual International Conference of the IEEE Engineering in Medicine and Biology Society, 2014, pp. 4735-4738.

Verma, et al., Multifocus Image Fusion Using Wavelet Transform, International Journal of Electronics and Computer Science Engineering, 2012, 1(4):2112-2118.

Xin, et al., Multi-Focus Image Fusion Based on the Nonsubsampled Contourlet Transform and Dual-Layer PCNN Model, Information Technology Journal, 2011, 10(6):1138-1149.

Zhang, et al., Multi-Focus Image Fusion with Sparse Feature Based Pulsed Coupled Neural Network, Telkomnika, 2014, 12(2):357-366.

Zheng, Pixel-Level Image Fusion Algorithms for Multi-Camera Imaging System, Master's Thesis, University of Tennessee, 2010, 97 pages.

Image Registration and Fusion Systems, Software Products, Copyright 2017, www.imgfsr.com/index.html, 4 pages.

* cited by examiner

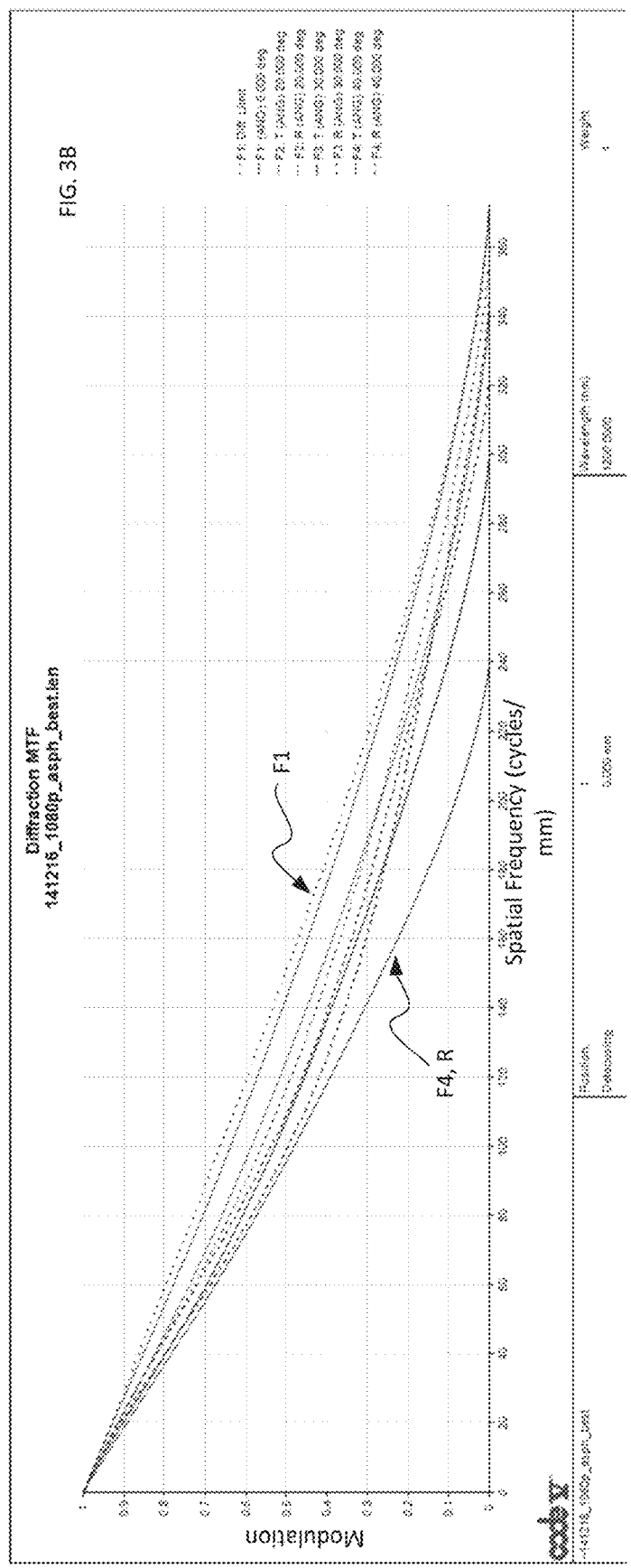

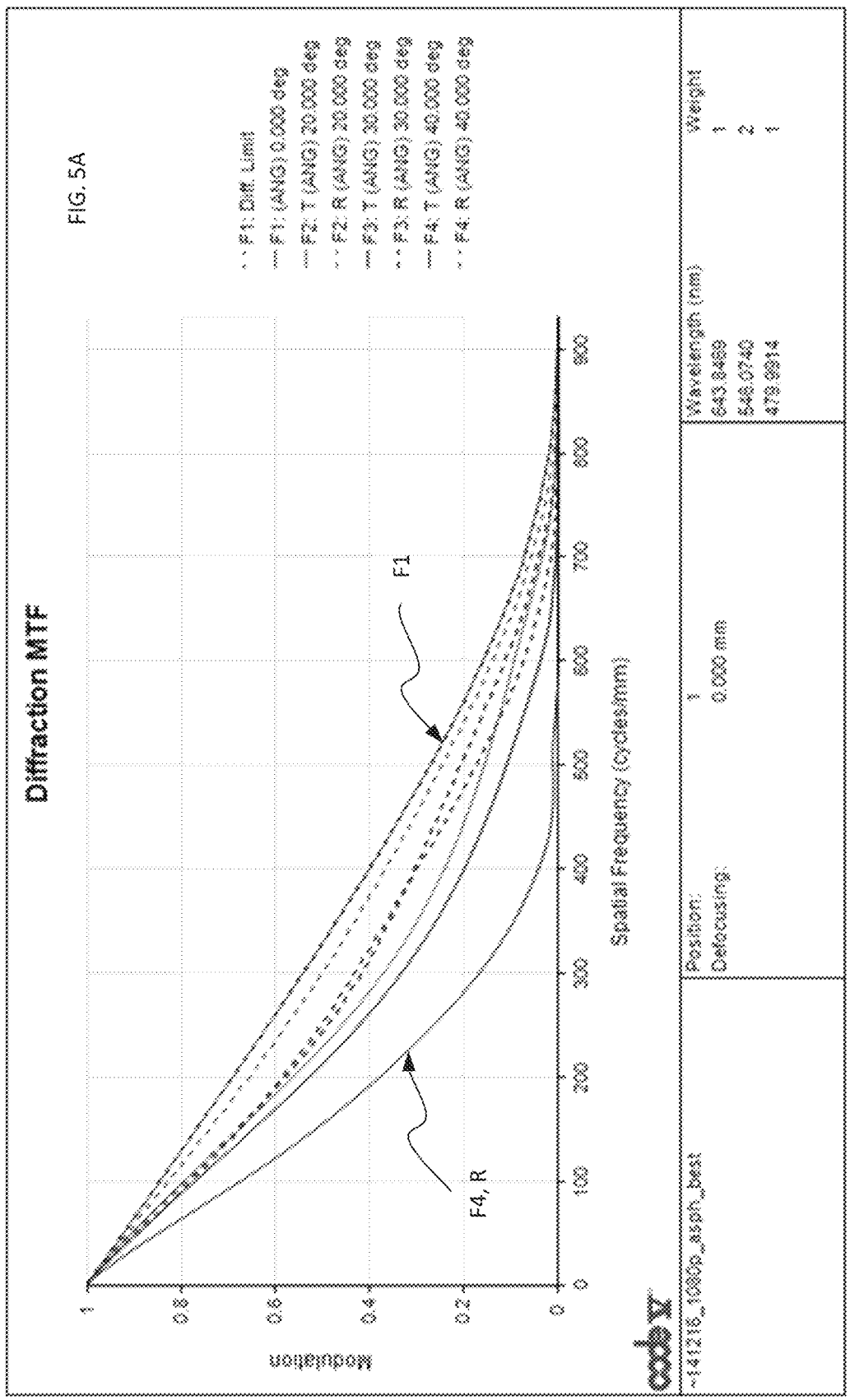

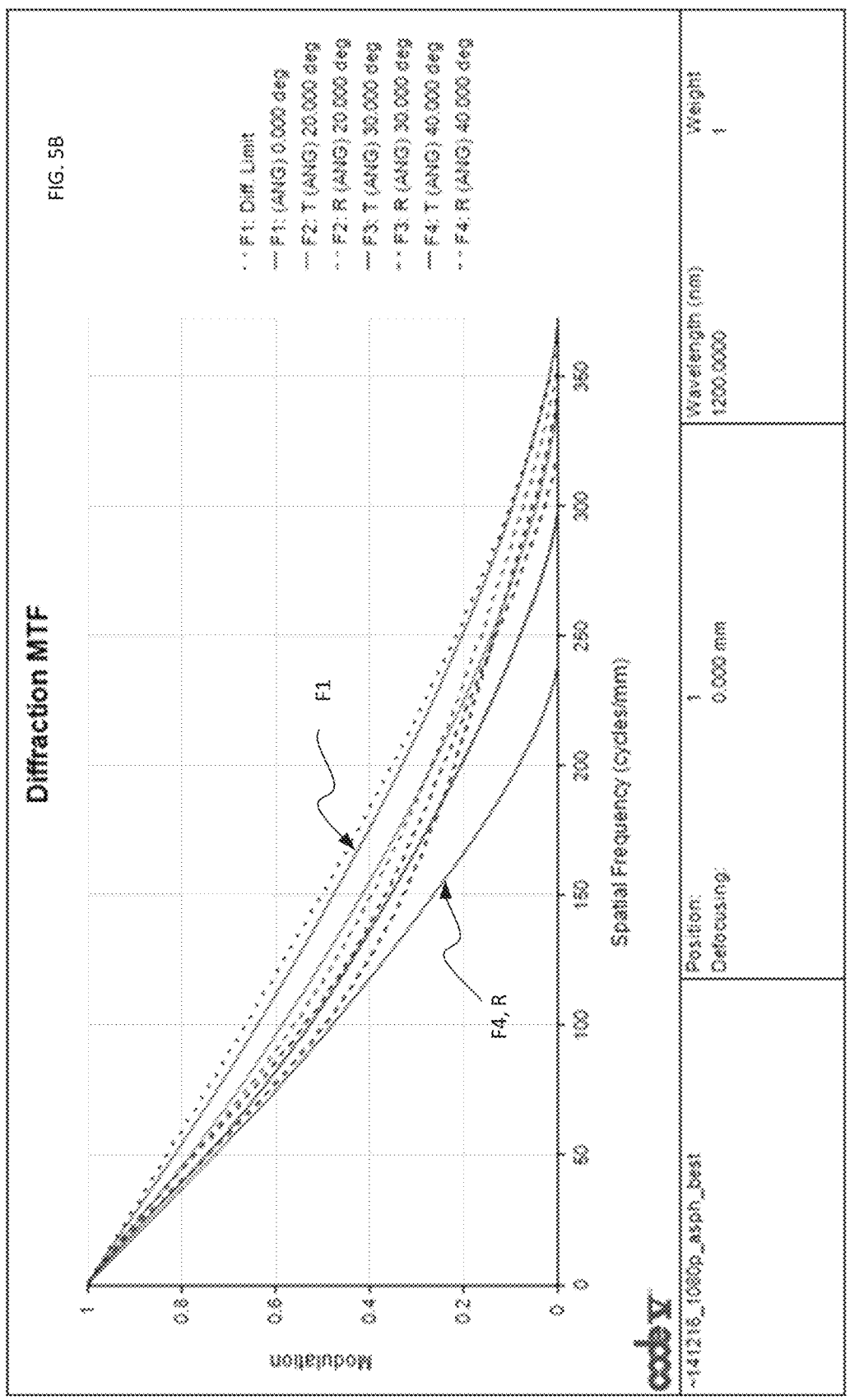

MULTISPECTRAL STEREOSCOPIC ENDOSCOPE SYSTEM AND USE OF SAME

CROSS-REFERENCE TO RELATED APPLICATIONS

This application claims priority from and benefit of a U.S. Provisional Application No. 62/277,328, filed on Jan. 11, 2016 and titled "Multi-Spectral Objectives and Stereoscopic Use Thereof", and U.S. Provisional Application No. 62/376,279 filed on Aug. 17, 2016 and titled "Multispectral Stereoscopic Endoscope System and Use of Same". The entire disclosure of each of these patent documents of incorporated herein by reference.

TECHNICAL FIELD

The present invention relates generally to formation of optical images based on optical data acquired with the use of an optical probe from the scene. In particular, the present invention relates to a multiple-channel optical endoscope system where different channels, while focused at different object distances, are configured to acquire data representing color-imagery in the visible portion of the optical spectrum through one channel and data representing monochromatic imagery in the visible portion of the optical spectrum and data representing near-IR imagery through another channel to provide resulting imagery for enhanced diagnostic use and depth-of-field once the different types of imaging data acquired with such system have been fused.

BACKGROUND

Endoscopes are often used in minimally invasive surgical procedures, such as laparoscopy, hysteroscopy, and colonoscopy, for example. Near-infrared (NIR) imaging using endoscopes has been described in the literature for various clinical applications. Often, such an imaging modality utilizes a contrast agent (such as indocyanine green, for example) that absorbs and/or fluoresces in the 700-900 nm range of the NIR. Although the preponderance of optical instruments currently in use are not optimized for both visible (VIS) and NIR light imaging, such instruments may still transmit sufficient NIR light that it may also be desirable to enable the previously described VIS-NIR imaging system for use with these conventional optical instruments. Conventional optical instruments are typically well-corrected for imaging throughout the visible spectrum, but without equivalent correction in the NIR, NIR images acquired with the aforementioned VIS-NIR imaging system through such optical instruments are likely to be of poor quality. Furthermore, although some of the NIR image aberrations introduced by conventional optical instruments may be corrected by applying compensating lens design techniques to the optical couplers, such techniques are typically not powerful enough to correct both the aberrations and the shift in focal plane between the visible and NIR images produced with such instruments.

Related art attempted to address some of the deficiencies by devising endoscope optics in which the imaging quality throughout the visible and NIR portions of the spectrum were balanced. This included examples of objective lenses (US 2008/0252997, US 2011/0002051; 2013/0057666) and a compensated optical coupler device (US 2011/0249323), to name just a few. While addressing some of existing deficiencies of the endoscope optics, these and other examples resemble each other in that they have substantially low apertures (typically corresponding to F/5 to F/11), which does not provide practically-sufficient diffraction-limited resolution for a wide-spectral-range imaging with sensor pixels dimensioned to about 1.5. microns. In addition, the existing solutions do not effectuate optical correction of monochromatic and chromatic aberrations, as well as barrel distortion, to a practically-acceptable low level.

Embodiments of related art remain deficient with respect to their ability to combine, or fuse, images received from multiple objectives of the same endoscopic probe while such objectives are optimized for operation at different object distances with the purpose of enhancing the diagnostic use and/or depth-of-field (DOF) as a result of simultaneous assessment of the images fused with the use of data-processing circuitry.

Embodiments of the present invention address these problems.

SUMMARY

An embodiment of the present invention provides a method for forming an image with an endoscope device. Such method includes transmitting light through a first group of lens elements of a first optical objective, disposed within a housing of an endoscope probe, onto an aperture stop located immediately adjacently to and after the first group of lens elements, where the first group of lens element has a first meniscus lens element and a first optical doublet. The method additionally includes transmitting light from the aperture stop through a second group of lens elements of the first optical objective to form an image at the image plane. The second group of lens elements includes a sequence of second, third, and fourth optical doublets. Here, the step of transmitting light through the first group of lens elements includes transmitting light through the first meniscus lens having a negative dioptric power. Alternatively or in addition, the step of transmitting light through the second group of lens elements includes transmitting light through a second meniscus lens positioned between the sequence of optical doublets and the second plane.

A related embodiment of the invention provides an endoscope probe which includes a tubular housing; and a first optical objective enclosed within such housing. The first optical objective contains coaxially-disposed first and second groups of lens elements, in which the first group of lens elements includes a first meniscus lens with a negative dioptric power and a first optical doublet; and the second group of lens elements includes a sequence of second, third, and fourth optical doublets and a second meniscus lens (having a positive dioptric power). An aperture stop is defined between the first and second optical doublets. In a specific embodiment, the endoscope probe may additionally comprise an optical fiber element disposed inside the tubular housing to collect light that has propagated through the first optical objective and reached a plane in which the image is formed, and to deliver so-collected light outside of the endoscope probe or at least to a distal end of the probe, towards the optical sensor. Or alternatively, in a related embodiment, an optical sensor is disposed at the image plane after the second meniscus lens element, inside the optical housing of the probe. Optionally, the first optical objective is telecentric in image space. In a specific case, at least one of the first and second groups of lens elements includes an aspheric refractive surface. An endoscope probe may include at least one more optical objective, providing optical data representing, in operation, the same scene as that imaged by the first optical objective to form an image that is different from the image formed with the first objective with respect to at least one optical characteristic. For example, two identical optical objectives may be with their axes being parallel to one another inside the same tubular housing of the probe.

BRIEF DESCRIPTION OF THE DRAWINGS

The invention will be more fully understood by referring to the following Detailed Description in conjunction with the generally not-to-scale schematic Drawings, of which:

FIG. 3B shows plots representing a portion of the MTF describing the operation of the embodiment of FIG. 2A at 1200 nm;

FIG. 5A shows plots representing a portion of the modulated transfer function (MTF) describing the operation of the embodiment of FIG. 4A in the visible portion of optical spectrum;

FIG. 5B shows plots representing a portion of the MTF describing the operation of the embodiment of FIG. 2A at 1200 nm;

Generally, the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

It is appreciated that embodiments of the present invention address the problems associated with devising a stereoscopic version of the endoscope (such as, for example, a stereoscopic laparoscopic system) that is required to simultaneously have high spatial resolution and operate in a broad spectral band. The solution to such problem is provided in a form of a fast telecentric objective lens design with (a high F/number telecentric objective lens) characterized by low vignetting, low distortion, and low chromatic aberrations that are substantially corrected across both the visible and the near infrared spectral bands.

This disclosure additionally describes a solution to the problem of achieving a high resolution imaging within a broad spectral band with the use of a stereoscopic endoscope system by configuring the multiple channels of such system in a specific fashion. In particular, one of the multiple channels is configured to provide color visible image information in one channel, and monochrome visible information in a second channel where the second channel also contains near infrared imaging information for enhanced diagnostic use and depth of field once the two imaging channels have been fused by image processing techniques.

EXAMPLE 1

Objectives for a Multi-Channel Endoscopic System

As known in the art, in some endoscopic imaging systems capable of high resolution simultaneous color and NIR imaging, none of the image sensors (if multiple image sensors are used) or specific pixels of an image sensor (if only a single color image sensor is used) are exclusively dedicated to NIR imaging. One exemplary imaging system utilizes a red, green, blue (RGB) sensor assembly to acquire both color and NIR fluorescence images by employing the red image sensor to, alternately and in rapid succession, acquire both the red light required for the color image and NIR light required for the NIR image. This imaging system is intended to be used in conjunction with image-projecting optical instruments such as endoscopes, microscopes, colposcopes, etc. that have also been optimized for both visible light and NIR imaging applications. Specifically, the optical instruments (i.e. endoscopes, microscopes, colposcopes, etc.) and the optical assemblies (optical couplers) that couple these instruments to the sensor assembly of the imaging system are constructed using appropriate visible and NIR transmitting optical materials and antireflection coatings and are optically designed to transmit visible and NIR images for which chromatic and geometric aberrations are minimized.

Figure 1:
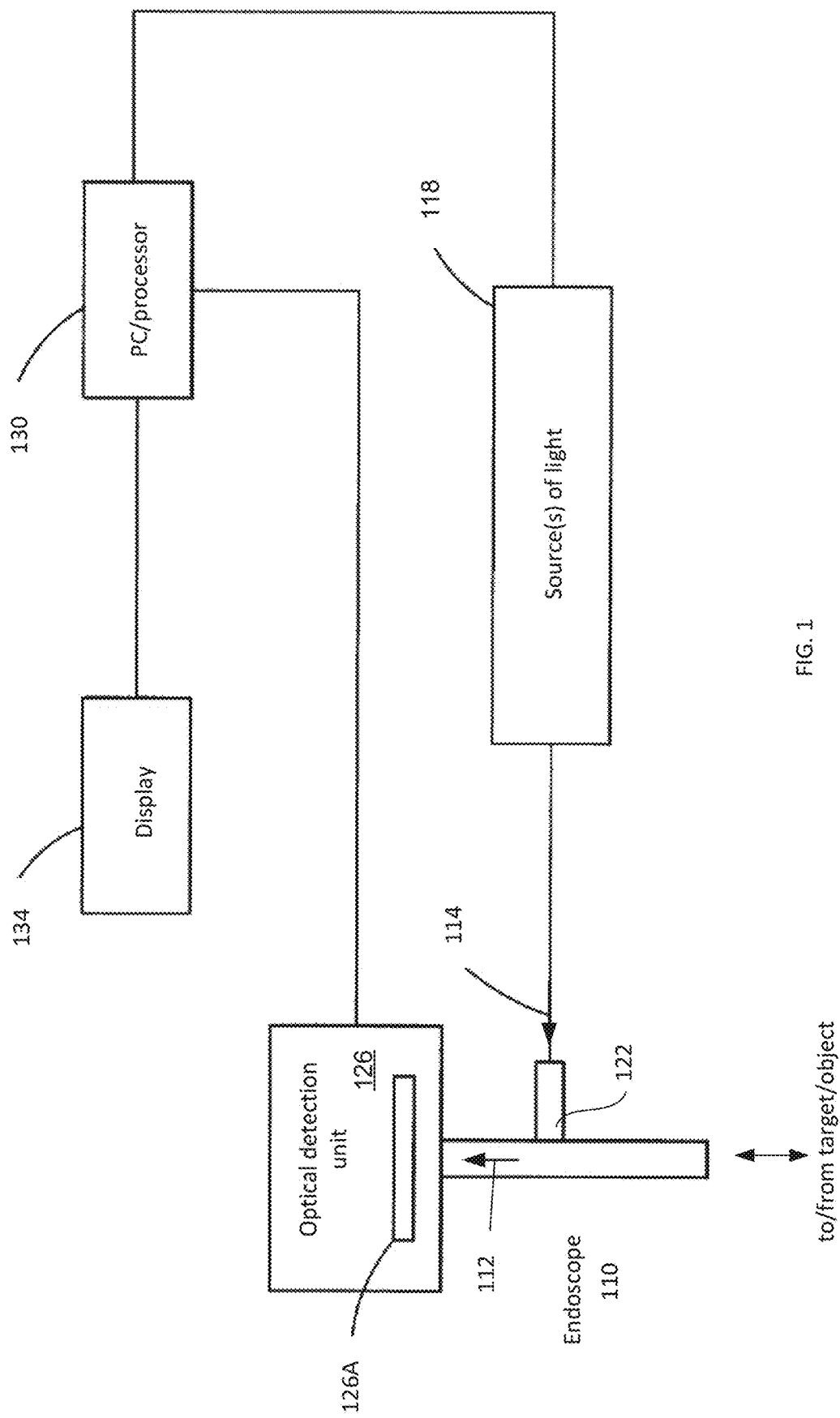
FIG. 1 is a schematic diagram of an endoscope-based optical imaging system.

FIG. 1 depicts a typical schematic configuration of an overall optical instrument 100 (an endoscope-employing optical imaging system) with which an embodiment of the invention can be utilized. Embodiment 100 representing an optical imaging system that employs an endoscope/optical probe 110 configured to collect and deliver light 112 (received from the target in response to irradiation of the target with light 114 from the source(s) of light 118 via the optical coupler 122) to the optical detection unit 126 with the optical sensor 126A. Additional sub-systems may be present, depending on particular implementation of the instrument 100.

In practice, the endoscope 110 is placed in the proximity of a target or object (such as the subject's tissue, for example inside a natural or created opening in the subject). The system may have one or more illumination sources 118 (such as high-power laser diodes, for example). The light source 118 emits radiation having wavelengths in the visible and/or infrared portions of the spectrum. Infrared radiation delivered towards the target at predetermined wavelengths may excite a fluorescent dye that has been associated with (affixed or adhered to) the target and cause the fluorescent light to be emitted and collected by the objective of the endoscope 110. In one embodiment, imaging may be performed in multiple discrete spectral bands, for example in two distinct infrared bands, in the infrared spectral band and two visible bands, or in the two infrared and a visible spectral bands, to name just a few examples.

The operation of at least the source(s) of light 118 and the optical detection unit 126 is typically governed by judiciously-designed electronic circuitry that may include a programmable processor 130 in operable communication with tangible, non-transitory computer-readable storage medium carrying program code thereon. The processor 130 may be further configured to perform processing of data received from the optical detection unit 126, as directed by the program code on the storage medium, and to communicate these data and/or the results of the data processing to display system 134 (such as a monitor, for example) to display the data/results thereon.

In one implementation, light at both visible and infrared wavelengths is delivered from the sources 110 to the target (not shown). The one or more illumination sources 118 are configured in operable communication with the PC or programmable processor 130 configured to govern the operation of the sources 118, to collect optical data from the detection unit 126, and to process the collected data to acquire information about the target.

In one implementation, the illumination sources 118 are coupled to the existing fiber optics in the endoscope or wand or coupled to an external cannula embedded with fiber optics or containing a working channel with sufficient diameter to place a fiber optic or fiber optic probe for the transmission of light at an excitation wavelength towards the target/object. The endoscope itself may contain a working channel sufficiently large for a laser fiber to be inserted and in that case a supplementary cannula or sheath for an excitation source would not be required.

Figure 4A:
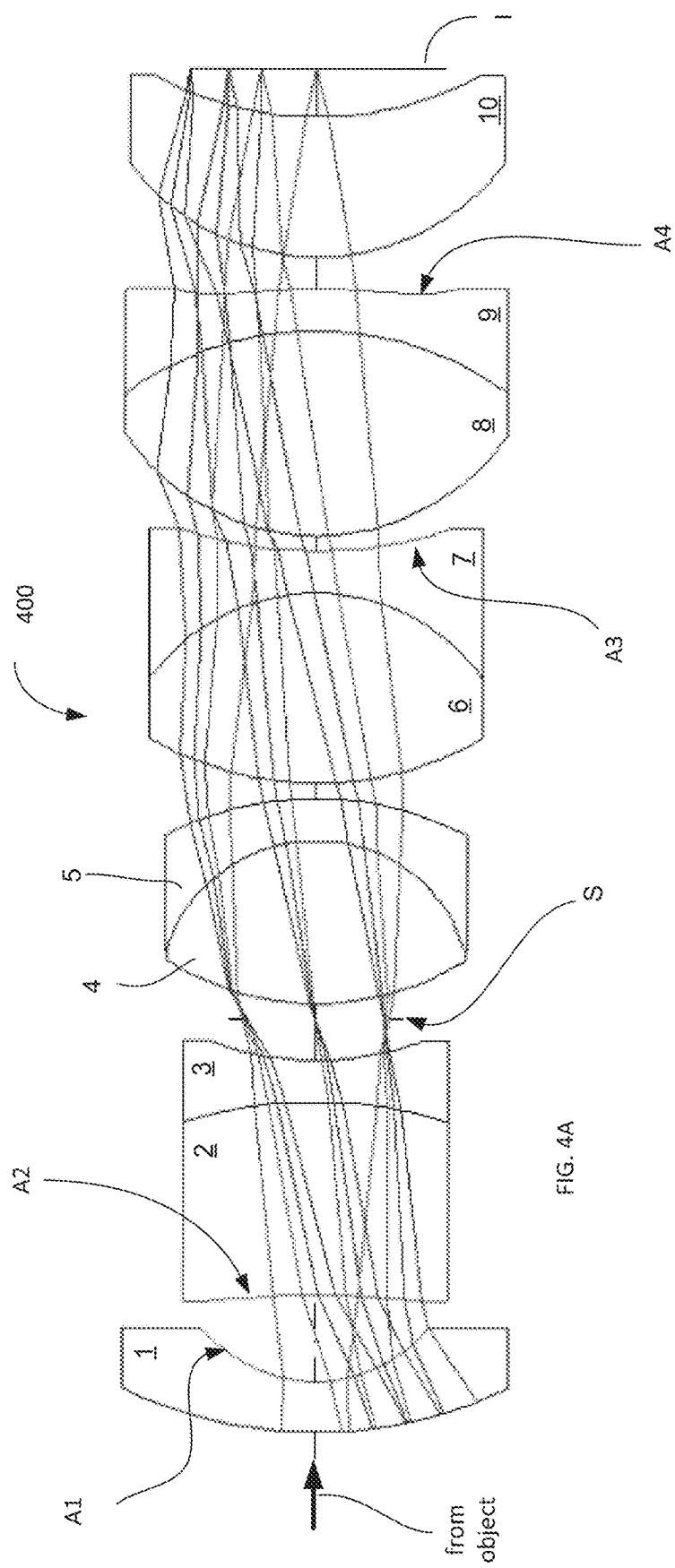
FIG. 4A is a diagram representing another embodiment of the optical objective of the endoscope probe of the system of FIG. 1.

Several notes are in order concerning an objective utilized in an embodiment of the endoscope of the invention. Tables 1A, 1B, 1C, 1D and 2A, 2B, 2C, 2D summarize the design prescriptions for embodiments of endoscope objectives that were performed with Code V and that are discussed in reference to corresponding Figures. In these Tables, optical elements and, possibly, media separating some of the elements, are numbered in a "backward" fashion, starting from that which is the closest to the object/target plane (to which light is delivered in operation from the source of light 118, FIG. 1) towards the plane of the optical sensor 126A. Such approach to numbering of the optical elements makes it easier, as would be appreciated by a skilled artisan, to define the NA and telecentricity in the image space—that is, in the space of the optical sensor—during the process of optical design. The closest to the object lens element is labeled as element 1 both in Table 1A and FIG. 2A (describing one embodiment of the objective) and in Table 2A and FIG. 4A (describing a related embodiment of the objective); the next lens elements is element 2 in each case, and so on, while the plane of the optical sensor is referred to as an image plane and labeled as "I". Positive radius value for a given surface indicates that the center of curvature of such surface is to the right of the surface, while a negative radius value indicates that the center of curvature is to the left of the surface; dimensions are provided in millimeters; thickness is defined as an axial distance from a given surface to the next surface; and an indicated image diameter is a paraxial value and not a ray-traced value. Furthermore, with respect to decentering constants, a decenter defines a new coordinate system (displaced and/or rotated) in which subsequent surfaces are defined. Surfaces following a decenter are aligned on the local mechanical axis (z-axis, for example) of the new coordinate system. The new mechanical axis remains in use for referencing purposes until expressly changed by another decenter. The order in which displacements and tilts are applied to a given surface is specified using different decenter types and these generate different new coordinate systems; those used in this disclosure are explained below. Alpha, beta, and gamma values are presented in degrees. Aspheric surfaces as labeled as $A_i$, and the aperture stop is denoted as S. Notations (both in drawings and description) referring to "R", "G", and "B" refer to wavelengths of about 643.85 nm, 546.1 nm, and 479.99 nm. Additionally, with respect to chromatic aberrations, a reduction in Strehl ratio between monochromatic and polychromatic designs represents the contrast loss from chromatic aberrations over the specified spectral band, while a variation in best individual focus shows the residual field curvature. In Tables, $n_d$ denotes a refractive index and $V_d$ denotes Abbe number at d-line of optical spectrum.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. When used in reference to a numerical value, represent a range of plus or minus 20% with respect to the specified value, more preferably plus or minus 10%, even more preferably plus or minus 5° %, most preferably plus or minus 2% with respect to the specified value.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes. In some specific cases, which are within the scope of the invention, the terms "approximately" and "about", when used in reference to a numerical value, represent a range of plus or minus 20% with respect to the specified value, more preferably plus or minus 10%, even more preferably plus or minus 5%, most preferably plus or minus 2% with respect to the specified value.

The presented optical designs provide an optical solution with low distortion, less than 1%. Low distortion, and well-corrected monochromatic and chromatic aberrations reduce the artifacts during image processing that would be needed to attempt equivalent image quality from an objective with larger aberrations. It also ensures that all of the pixels on the sensor are used efficiently, even those as small as 1.5 micron pitch, which enables a High Definition 720p or 1080p visible laparoscope with near infrared imaging capability limited primarily by diffraction at the longer wavelengths.

TABLE 1A

| ELEMENT NUMBER | RADIUS OF CURVATURE | | THICKNESS | $n_d$ | $v_d$ |
|---|---|---|---|---|---|
| | FRONT | BACK | | | |
| OBJECT | INF | | 49.8949 | | |
| 1 | 4.0634 CX | A(1) | 0.4838 | 1.75500 | 52.30 |
| | | | 0.8228 | | |
| 2 | A(2) | −4.1293 CX | 1.8347 | 1.84666 | 23.78 |
| 3 | −4.1293 CC | 2.8416 CC | 0.3992 | 1.45600 | 90.90 |
| | | | 0.3819 | | |
| | APERTURE STOP | | 0.1498 | | |
| 4 | 2.5557 CX | −1.4512 CX | 1.5536 | 1.52855 | 76.98 |
| 5 | −1.4512 CC | −3.0650 CX | 0.3992 | 1.64049 | 60.10 |
| | | | 0.1468 | | |
| 6 | 3.0872 CX | −1.8957 CX | 1.8073 | 1.45600 | 90.90 |
| 7 | −1.8957 CC | A(3) | 0.3992 | 1.65412 | 39.70 |
| | | | 0.1497 | | |
| 8 | 2.1566 CX | −2.9937 CX | 1.9418 | 1.52855 | 76.98 |
| 9 | −2.9937 CC | A(4) | 0.3992 | 1.75500 | 52.30 |
| | | | 0.2996 | | |
| 10 | 2.1584 CX | 3.1138 CC | 1.3306 | 1.61800 | 63.39 |
| | IMAGE DISTANCE = | | 0.4737 | | |
| IMAGE | INF | | (image height = 2.3922) | | |

NOTES - Positive radius indicates the center of curvature is to the right
Negative radius indicates the center of curvature is to the left
Dimensions are given in millimeters
Thickness is axial distance to next surface
Image diameter shown above is a paraxial value, it is not a ray traced value
Other glass suppliers can be used if their materials are functionally equivalent to the extent needed by the design; contact the designer for approval of substitutions.
aspheric constants $$Z = \frac{(CURV)Y^2}{1 + (1 - (1+K)(CURV)^2 Y^2)^{1/2}} + (A)Y^4 + (B)Y^6 + (C)Y^8 + (D)Y^{10}$$

| ASPHERIC | CURV | K | A | B | C | D |
|---|---|---|---|---|---|---|
| A(1) | 0.78558871 | 0.00000000 | −3.11053E−02 | −1.94017E−02 | 1.35480E−03 | 0.00000E+00 |
| A(2) | −0.12033603 | 0.00000000 | −6.35979E−03 | 2.55200E−03 | 7.70975E−03 | 0.00000E+00 |
| A(3) | 0.25606358 | 0.00000000 | 1.52703E−04 | −6.39236E−05 | 4.26605E−04 | 0.00000E+00 |
| A(4) | −0.15216745 | 0.00000000 | 3.24254E−02 | 4.41790E−03 | 1.31113E−03 | 0.00000E+00 |

REFERENCE WAVELENGTH = 546.1 NM
SPECTRAL REGION = 480.0-643.8 NM

INFINITE CONJUGATES
EFL = 1.4400
BFL = 0.4334
FFL = 1.6136
F/NO = 2.2190
AT USED CONJUGATES
REDUCTION = 0.0280
FINITE F/NO = 2.2187
OBJECT DIST = 49.8949
TOTAL TRACK = 62.8676
IMAGE DIST = 0.4737
OAL = 12.4990
PARAXIAL
IMAGE HT = 1.2072
IMAGE DIST = 0.4737
SEMI-FIELD
ANGLE = 40.0000
ENTR PUPIL
DIAMETER = 0.6489
DISTANCE = 1.6053

TABLE 1A-continued

|  | EXIT PUPIL |  |
|---|---|---|
| DIAMETER = | | 113.5741 |
| DISTANCE = | | 252.4582 |

NOTES - FFL is measured from the first surface
BFL is measured from the last surface

TABLE 1B

POLYCHROMATIC WAVEFRONT ANALYSIS OVER VISIBLE SPECTRUM

| | | | | |
|---|---|---|---|---|
| X REL. FIELD | 0.00 | 0.00 | 0.00 | 0.00 |
| Y REL. FIELD | 0.00 | 0.43 | 0.69 | 1.00 |
| WEIGHTS | 1.00 | 1.00 | 1.00 | 1.00 |
| NUMBER OF RAYS | 948 | 838 | 710 | 558 |
| WAVELENGTHS | 643.8 | 546.1 | 480.0 | |
| WEIGHTS | 1 | 2 | 1 | |

| | | | BEST INDIVIDUAL FOCUS | | | | BEST COMPOSITE FOCUS | | |
|---|---|---|---|---|---|---|---|---|---|
| | FIELD | | SHIFT | FOCUS | RMS | | SHIFT | FOCUS | RMS |
| | FRACT | DEG | (MM.) | (MM.) | (WAVES) | STREHL | (MM.) | (MM.) | (WAVES) | STREHL |
| X | 0.00 | 0.00 | 0.000000 | 0.000017 | 0.0033 | 1.000 | 0.000000 | −0.000073 | 0.0036 | 0.999 |
| Y | 0.00 | 0.00 | 0.000000 | | | | 0.000000 | | | |
| X | 0.00 | 0.00 | 0.000000 | 0.000372 | 0.0438 | 0.927 | 0.000000 | −0.000073 | 0.0441 | 0.926 |
| Y | 0.43 | 20.00 | −0.000097 | | | | −0.000105 | | | |
| X | 0.00 | 0.00 | 0.000000 | −0.001199 | 0.0446 | 0.925 | 0.000000 | −0.000073 | 0.0462 | 0.919 |
| Y | 0.6 | 30.01 | −0.000028 | | | | 0.000005 | | | |
| X | 0.00 | 0.00 | 0.000000 | 0.000287 | 0.0655 | 0.844 | 0.000000 | −0.000073 | 0.0655 | 0.844 |
| Y | 1.00 | 40.01 | 0.000149 | | | | 0.000148 | | | |

COMPOSITE RMS FOR POSITION 1: 0.04264
Units of RMS are waves at 534.3 nm.
NOTE
Strehl is the intensity at the peak of the point image as a fraction of the peak of the aberration-free image with the same vignetting and obscuration. The approximation used here is generally valid for RMS <0.1.

TABLE 1C

MONOCHROMATIC WAVEFRONT ANALYSIS AT 546.1 nm WAVELENGTH

| | | | | |
|---|---|---|---|---|
| X REL. FIELD | 0.00 | 0.00 | 0.00 | 0.00 |
| Y REL. FIELD | 0.00 | 0.43 | 0.69 | 1.00 |
| WEIGHTS | 1.00 | 1.00 | 1.00 | 1.00 |
| NUMBER OF RAYS | 316 | 280 | 236 | 186 |
| WAVELENGTHS | 643.8 | 546.1 | 480.0 | |
| WEIGHTS | 0 | 1 | 0 | |

| | | | BEST INDIVIDUAL FOCUS | | | | BEST COMPOSITE FOCUS | | |
|---|---|---|---|---|---|---|---|---|---|
| | FIELD | | SHIFT | FOCUS | RMS | | SHIFT | FOCUS | RMS |
| | FRACT | DEG | (MM.) | (MM.) | (WAVES) | STREHL | (MM.) | (MM.) | (WAVES) | STREHL |
| X | 0.00 | 0.00 | 0.000000 | 0.000027 | 0.0012 | 1.000 | 0.000000 | −0.000153 | 0.0028 | 1.000 |
| Y | 0.00 | 0.00 | 0.000000 | | | | 0.000000 | | | |
| X | 0.00 | 0.00 | 0.000000 | 0.000198 | 0.0333 | 0.957 | 0.000000 | −0.000153 | 0.0335 | 0.951 |
| Y | 0.43 | 20.00 | −0.000138 | | | | −0.000144 | | | |
| X | 0.00 | 0.00 | 0.000000 | −0.001364 | 0.0335 | 0.957 | 0.000000 | −0.000153 | 0.0358 | 0.951 |
| Y | 0.69 | 30.00 | −0.000135 | | | | −0.000100 | | | |
| X | 0.00 | 0.00 | 0.000000 | 0.000242 | 0.0278 | 0.970 | 0.000000 | −0.000153 | 0.0280 | 0.969 |
| Y | 1.00 | 40.00 | −0.000178 | | | | −0.000180 | | | |

COMPOSITE RMS FOR POSITION 1: 0.02145
Units of RMS are waves at 546.1 nm.
NOTE
Strehl is the intensity at the peak of the point image as a fraction of the peak of the aberration-free image with the same vignetting and obscuration. The approximation used here is generally valid for RMS <0.1.

TABLE 1D

MONOCHROMATIC WAVEFRONT ANALYSIS AT 1200 nm WAVELENGTH

| X REL. FIELD | 0.00 | 0.00 | 0.00 | 0.00 |
|---|---|---|---|---|
| Y REL. FIELD | 0.00 | 0.43 | 0.69 | 1.00 |
| WEIGHTS | 1.00 | 1.00 | 1.00 | 1.00 |
| NUMBER OF RAYS | 316 | 280 | 236 | 186 |
| WAVELENGTHS | 1200.0 | | | |
| WEIGHTS | 1 | | | |

| | | | BEST INDIVIDUAL FOCUS | | | BEST COMPOSITE FOCUS | | | |
|---|---|---|---|---|---|---|---|---|---|
| FIELD | | SHIFT | FOCUS | RMS | | SHIFT | FOCUS | RMS | |
| FRACT | DEG | (MM.) | (MM.) | (WAVES) | STREHL | (MM.) | (MM.) | (WAVES) | STREHL |
| X 0.00 | 0.00 | 0.000000 | −0.003425 | 0.0063 | 0.998 | 0.000000 | −0.005192 | 0.0126 | 0.994 |
| Y 0.00 | 0.00 | 0.000000 | | | | 0.000000 | | | |
| X 0.00 | 0.00 | 0.000000 | −0.005794 | 0.0155 | 0.991 | 0.000000 | −0.005192 | 0.0158 | 0.990 |
| Y 0.43 | 20.00 | −0.000482 | | | | −0.000473 | | | |
| X 0.00 | 0.00 | 0.000000 | −0.008030 | 0.0212 | 0.982 | 0.000000 | −0.005192 | 0.0250 | 0.976 |
| Y 0.69 | 30.00 | −0.000753 | | | | −0.000673 | | | |
| X 0.00 | 0.00 | 0.000000 | −0.005657 | 0.0278 | 0.970 | 0.000000 | −0.005192 | 0.0279 | 0.970 |
| Y 1.00 | 40.00 | −0.000823 | | | | −0.000821 | | | |

COMPOSITE RMS FOR POSITION 1: 0.02013
Units of RMS are waves at 1200.0 nm.
NOTE
Strehl is the intensity at the peak of the point image as a fraction of the peak of the aberration-free image with the same vignetting and obscuration. The approximation used here is generally valid for RMS <0.1.

Figure 2A:
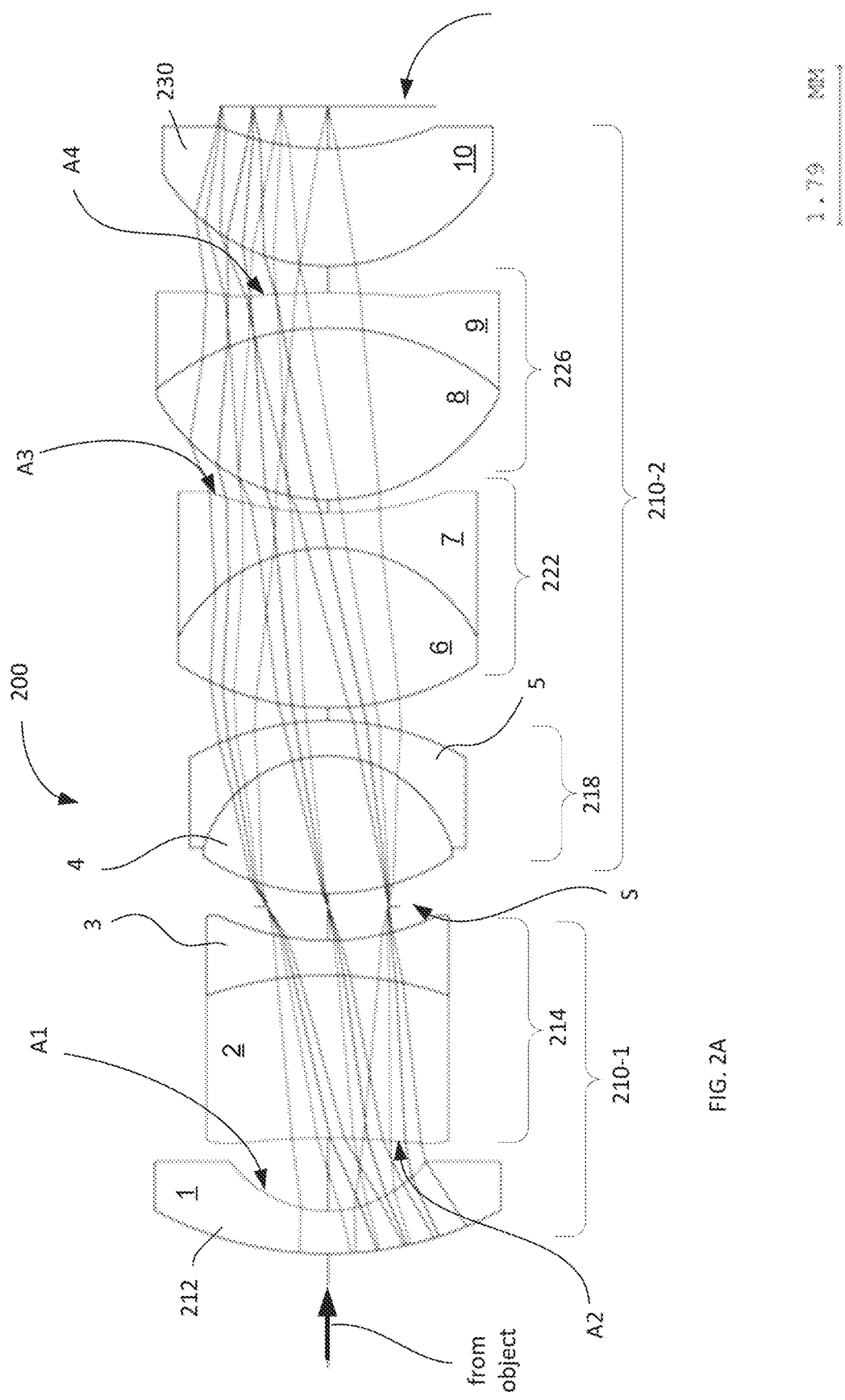
FIG. 2A is a diagram representing an embodiment of the optical objective of the endoscope probe of the system of FIG. 1.

Tables 1A, 1B, 1C, and 1D provide data representing an optical train (sequence) of lens elements of an embodiment 200 of FIG. 2A, forming a multispectral endoscope objective.

A specific example 200 of the objective structured as described in the above Tables 1A through 1D has an effective focal length of 1.44 mm, which results (for a full diagonal field of view of 80 degrees and in the absence of significant distortion) in formation of an image across a 2.4 mm diagonal rectangular active area on an optical sensor 126A. The F/number achieved in this design is about 2.2, which (in operation at a wavelength of 550 nm) enables a diffraction-limited Airy disc with a diameter of the first dark ring of 1.5 microns; and twice that, 3.0 microns, during the operation of the objective at a 1100 nm wavelength. In order to implement a stereoscopic system in an endoscope device, two of these objectives are used in parallel, with two sensors (126A and another, not shown), each receiving optical from a corresponding objective at the optical detection unit. For example, in the case of the two sensors, the optical detection unit includes a first optical sensor configured to received and detect the visible light and a second optical sensor configured to receive and detect the infrared light.

The optical objective 200 includes first and second groups of lens elements, where the first group 210-1 of lens elements includes a first meniscus lens 212 (element 1) with a negative dioptric power and a first optical doublet 214; and the second group 210-2 of lens elements, which includes a sequence of second, third, and fourth optical doublets 218, 222, 226 and a second meniscus lens 230 (element 10). The aperture stop A is defined between the first and second optical doublets. 214, 218. Generally, at least one of the first and second groups 210-1, 210-2 of lens elements of the endoscope objective configured according to the idea of the invention includes an aspheric refractive surface. In a specific embodiment of FIG. 2A, there are two aspheric surfaces in each of the first and second groups of lens elements 210-1, 210-2.

Accordingly, a process of formation of an image with the use of the endoscope containing the embodiment 200 of the objective includes the steps of (i) transmitting light through a first group of lens elements of a first optical objective disposed within a housing of an endoscope to form an intermediate image at a first plane defined by an aperture stop of the first optical objective (where the first group has a first meniscus lens element and a first optical doublet) and (ii) transmitting light from the intermediate image through a second group of lens elements of the first optical objective to form a first resulting image at a second plane (where the second group including a sequence of second, third, and fourth optical doublets). In doing so, transmitting light through the first group of lens elements includes transmitting light through the first meniscus lens having a positive dioptric power while transmitting light through the second group of lens elements includes transmitting light through a second meniscus lens positioned between the sequence of identified optical doublets and the second plane.

The image formed with the use of a single objective such as that of FIG. 2A (or a stereo-image formed with the use of two objectives 200) geometrically matches a 720p high-definition visible sensor with 1.5 micron pixel pitch, and/or a half-720p near infrared sensor. There is no vignetting at the aperture stop, disposed between the first and second groups of the lens elements, and the objective is approximately telecentric at the sensor plane (thereby minimizing illumination non-uniformity and loss of resolution across the field of view, especially when used with a sensor without a microlens array covering the pixels). The objective has four aspheric (up to the 6th power, as shown in Table 1A) surfaces, shown as A1, A2, A3, and A4 (in red line) in FIG. 2A.

Figure 2B:
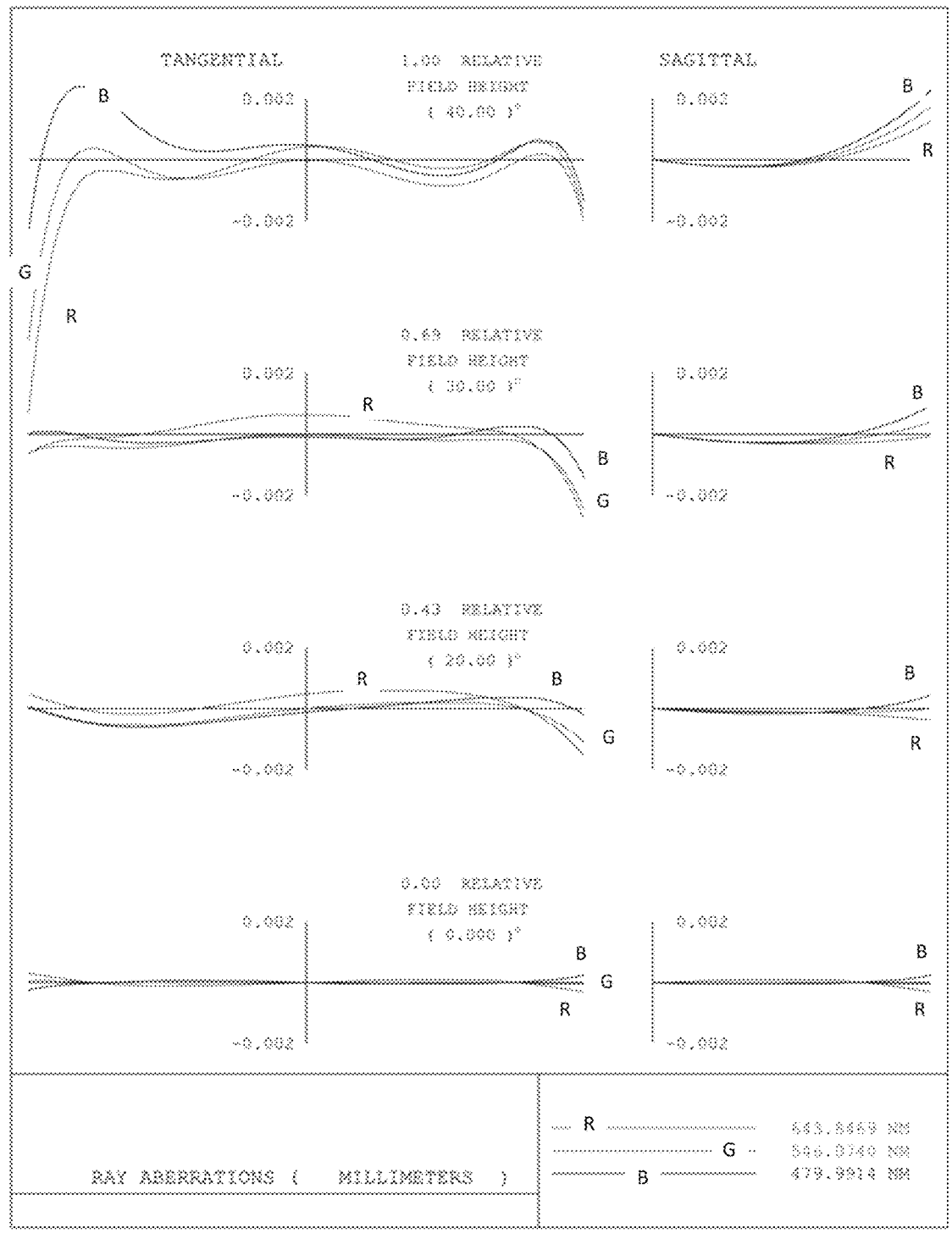
FIG. 2B contains plots illustrating ray aberrations characterizing the design of the embodiment of FIG. 2A; plots labeled "R", "G", and "B" represent, respectively, ray aberrations at about 643.85 nm, 546.1 nm, and 479.99 nm wavelengths.
Figure 2C:
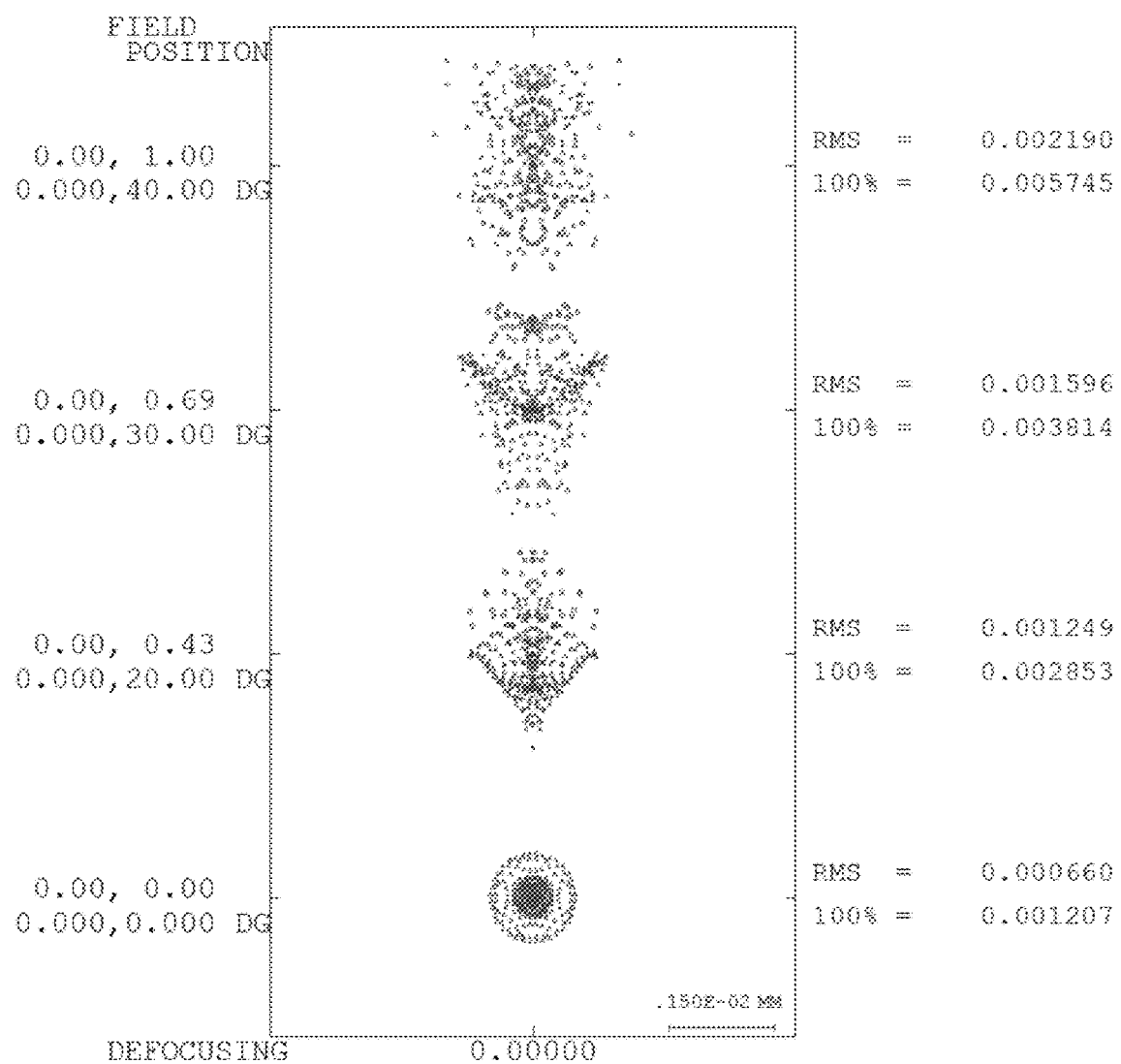
FIG. 2C shows the spot diagrams characterizing imaging at R, G, and B wavelengths with the use of the embodiment of FIG. 2A.
Figure 2D:
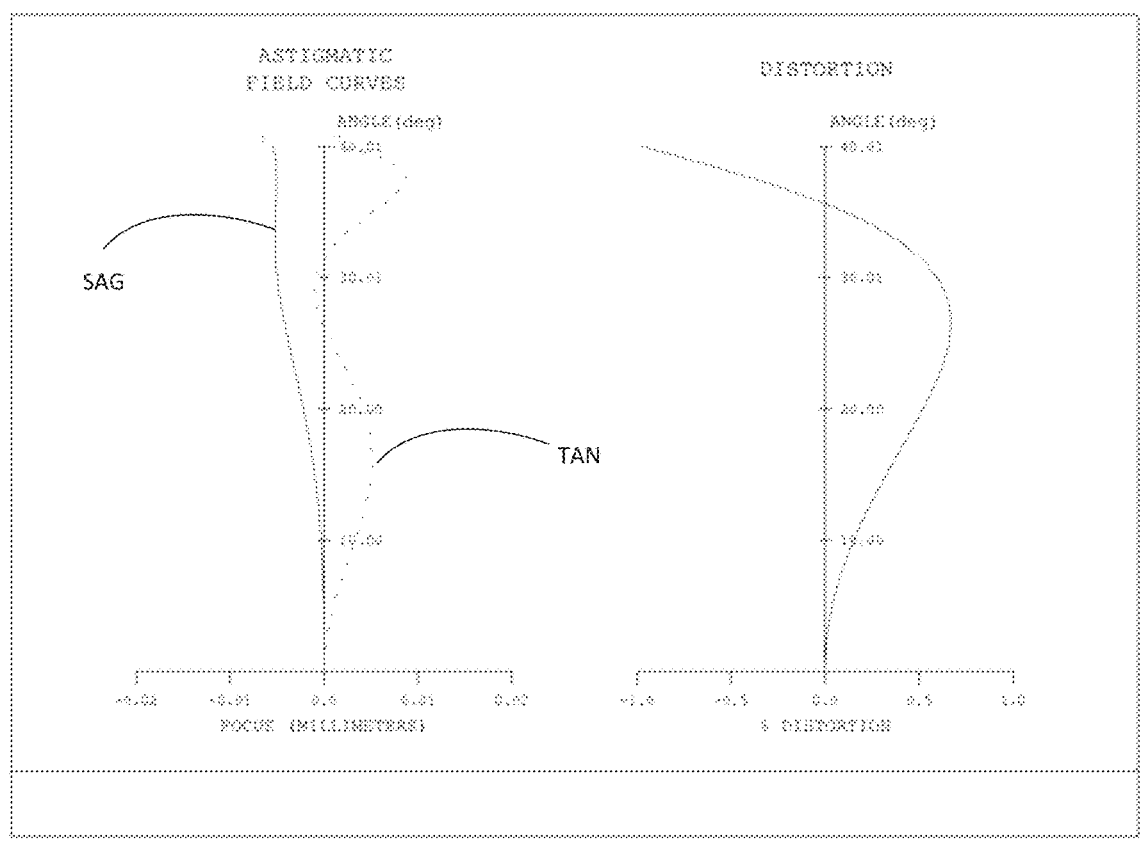
FIG. 2D presents field curves and a distortion curve characterizing the imaging properties of the embodiment of FIG. 2A.

FIGS. 2B, 2C illustrate ray aberrations and spot diagrams representing optical performance of the embodiment 200. The distortion figure is notably within 1% for field angles up to 40 degrees (FIG. 2D). Lateral color over the visible range (or at least within the range of wavelengths between about 480 nm and 643 nm) has a value comparable to the dimension of 1 pixel—or about 1.5 microns and, in practice, the possible increase of the lateral color aberration with increase in operational wavelength is corrected with the use of software processing optical images acquired by the sensor 126A.

Geometrical dimensions summarized in Table 1A evidence the practical compatibility of the objective design with dimensional requirements of the endoscope devices. The polychromatic analysis of performance of the embodiment over the visible portion of the spectrum, Table 1B, evidences that the operation of the objective is reliably characterized by a first Strehl ratio at the central wavelength (546.1 nm) and a second Strehl ratio across the chosen spectral bandwidth (in this example: 480.0 nm . . . 643.8 nm), both of which exceed 0.844 for the fields up to 40 degrees. At the same time, the polychromatic (second) Strehl ratio exceeds 0.92 for any field up to 20 degrees, while still remaining above 0.90 for any field up to 30 degrees. At any value of the field angle up to 40 degrees the ratio of the Strehl ratio at a central wavelength to the Strehl ratio across the chosen visible bandwidth exceeds unity and, in this example, is within the range between about 1.0010 and about 1.1848. The monochromatic analysis of the performance of the embodiment over the visible portion of the spectrum, Table 1C, evidences that the operation of the objective is reliably characterized by the individual Strehl ratio (at the central wavelength chosen to be 546.1 nm) remaining at a value of at least 0.970 for any field up to 40 degrees, and higher than 0.95 for any field up to 30 degrees.

At the same time or alternatively, the wavefront analysis in the IR portion of the spectrum (Table 1D) shows that the operation of the embodiment 200 simultaneously exhibits the individual Strehl ratio (at the chosen IR wavelength) exceeding or equal to at least 0.970 for any field angle up to 40 degrees, while remaining above 0.99 for any field angle up to 20 degrees.

Notably, in one embodiment the endoscope probe objective is telecentric at the sensor (in the image space), to accommodate an implementation in which an endoscope optical sensor may not be able to tolerate a wide range of angle of incidence and is optionally complemented with an array of microlenses separating the objective from the sensor.

It is understood that a telecentric lens is a compound lens that has its entrance or exit pupil at infinity at an infinite distance from such lens). Accordingly, the chief rays (oblique rays that pass through the center of the aperture stop) are parallel to the optical axis of such lens either in front of or behind the lens, respectively. An exit pupil at infinity makes the lens image-space telecentric. An image-space telecentric objective produces images of the same size regardless of the distance between the lens and the optical sensor 126A. This allows the objective of the invention to be focused to different distances without changing the size of the image.

In practice, the endoscope probe of the device of the invention may be configured by optically complementing the objective 200 (in a mono-embodiment) or a pair of objectives 200 (in a stereo-embodiment of the probe) with corresponding optical fiber elements (such as multimode optical fiber(s), MMFs, or large-dimensions fiber-optic-bundle lightguides; not shown in FIG. 2A) the entrance end facets of which have optical quality and disposed at the image plane I to collect light received from the object through the endoscope probe objective at the image plane and relay the formed image to the corresponding optical sensor. At least a portion of each optical fiber element is disposed within the endoscope probe tubular housing—just like the objectives themselves—and further extends in a sheath towards the optical detection unit 126. In this case, the formation of image with the embodiment of the endoscope additionally includes transmitting light received at the second plane from the objective of the endoscope through an optical fiber element towards an associated optical sensor.

Figure 3A:
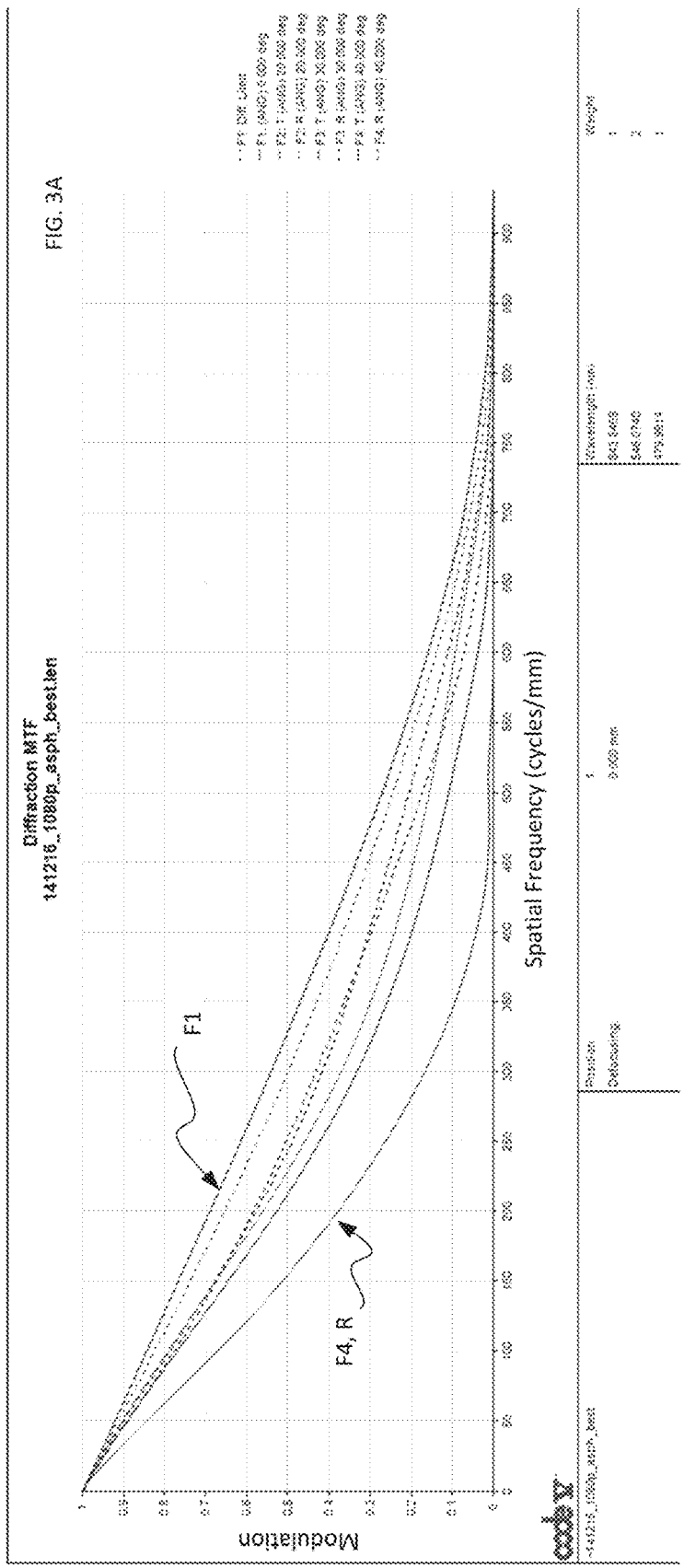
FIG. 3A shows plots representing a portion of the modulated transfer function (MTF) describing the operation of the embodiment of FIG. 2A in the visible portion of optical spectrum.

FIGS. 3A and 3B illustrate parameters of the modulated transfer function (MTF) characterizing the operation of the embodiment 200 in the visible portion of the spectrum and in light at 1200 nm, respectively, evidencing that the cut-off frequency in the visible portion of the spectrum is always above about 575 cycles/mm (both for imaging in tangential and sagittal planes, and exceeding 750 cycles/mm for imaging in sagittal plane) at any field angle up to 40 degrees, while, simultaneously, being maintained above about 240 cycles/mm both for imaging in tangential and sagittal planes, and reaching about 340 cycles/mm for imaging in sagittal plane) at 1200 nm.

TABLE 2A

| ELEMENT NUMBER | RADIUS OF CURVATURE | | THICKNESS | $n_d$ | $v_d$ |
|---|---|---|---|---|---|
| | FRONT | BACK | | | |
| OBJECT | INF | | 81.9420 | | |
| 1 | 6.6733 CX | A(1) | 0.7945 | 1.75500 | 52.30 |
| | | | 1.3512 | | |
| 2 | A(2) | −6.7815 CX | 3.0131 | 1.84666 | 23.78 |
| 3 | −6.7815 CC | 4.6671 CC | 0.6555 | 1.45600 | 90.90 |
| | | | 0.6272 | | |
| | APERTURE STOP | | | | |
| 4 | 4.1972 CX | −2.3834 CX | 2.5515 | 1.52855 | 76.98 |
| 5 | −2.3834 CC | −5.0337 CX | 0.6555 | 1.64049 | 60.10 |
| | | | 0.2411 | | |
| 6 | 5.0701 CX | −3.1133 CX | 2.9682 | 1.45600 | 90.90 |
| 7 | −3.1133 CC | A(3) | 0.6555 | 1.65412 | 39.70 |
| | | | 0.2458 | | |

TABLE 2A-continued

| | | | | | |
|---|---|---|---|---|---|
| 8 | 3.5418 CX | −4.9165 CX | 3.1890 | 1.52855 | 76.98 |
| 9 | −4.9165 CC | A(4) | 0.6555 | 1.75500 | 52.30 |
| | | | 0.4920 | | |
| 10 | 3.5446 CX | 5.1137 CC | 2.1853 | 1.61800 | 63.39 |
| | IMAGE DISTANCE = | | 0.7779 | | |
| IMAGE | INF | | | (image height = 2.3922) | |

NOTES - Positive radius indicates the center of curvature is to the right
Negative radius indicates the center of curvature is to the left
Dimensions are given in millimeters
Thickness is axial distance to next surface
Image diameter shown above is a paraxial value, it is not a ray traced value
Other glass suppliers can be used if their materials are functionally equivalent to the extent needed by the design; contact the designer for approval of substitutions.
aspheric constants $$Z = \frac{(CURV)Y^2}{1 + (1 - (1 + K)(CURV)^2 Y^2)^{1/2}} + (A)Y^4 + (B)Y^6 + (C)Y^8 + (D)Y^{10}$$

| ASPHERIC | CURV | K | A | B | C | D |
|---|---|---|---|---|---|---|
| A(1) | 0.47834908 | 0.00000000 | −7.02237E−03 | −1.62401E−03 | 4.20459E−05 | 0.00000E+00 |
| A(2) | −0.07327324 | 0.00000000 | −1.43579E−03 | 2.13614E−04 | 2.39270E−04 | 0.00000E+00 |
| A(3) | 0.15591845 | 0.00000000 | 3.44743E−05 | −5.35069E−06 | 1.32396E−05 | 0.00000E+00 |
| A(4) | −0.09265555 | 0.00000000 | 7.32039E−03 | 3.69798E−04 | 4.06906E−05 | 0.00000E+00 |

REFERENCE WAVELENGTH = 546.1 NM
SPECTRAL REGION = 480.0 – 643.8 NM

| | | |
|---|---|---|
| INFINITE CONJUGATES | | |
| EFL = | | 2.3648 |
| BFL = | | 0.7118 |
| FFL = | | 2.6500 |
| F/NO = | | 2.2190 |
| AT USED CONJUGATES | | |
| REDUCTION = | | 0.0280 |
| FINITE F/NO = | | 2.2187 |
| OBJECT DIST = | | 81.9420 |
| TOTAL TRACK = | | 103.2469 |
| IMAGE DIST = | | 0.7779 |
| OAL = | | 20.5270 |
| PARAXIAL | | |
| IMAGE HT = | | 1.9826 |
| IMAGE DIST = | | 0.7779 |
| SEMI-FIELD | | |
| ANGLE = | | 40.0000 |
| ENTR PUPIL | | |
| DIAMETER = | | 1.0657 |
| DISTANCE = | | 2.6364 |
| EXIT PUPIL | | |
| DIAMETER = | | 186.5218 |
| DISTANCE = | | 414.6100 |

NOTES - FFL is measured from the first surface
BFL is measured from the last surface

TABLE 2B

POLYCHROMATIC WAVEFRONT ANALYSIS OVER VISIBLE SPECTRUM

| | | | | |
|---|---|---|---|---|
| X REL. FIELD | 0.00 | 0.00 | 0.00 | 0.00 |
| Y REL. FIELD | 0.00 | 0.43 | 0.69 | 1.00 |
| WEIGHTS | 1.00 | 1.00 | 1.00 | 1.00 |
| NUMBER OF RAYS | 948 | 838 | 698 | 542 |
| WAVELENGTHS | 643.8 | 546.1 | 480.0 | |
| WEIGHTS | 1 | 2 | 1 | |

| | | | BEST INDIVIDUAL FOCUS | | | BEST COMPOSITE FOCUS | | | |
|---|---|---|---|---|---|---|---|---|---|
| FIELD | | SHIFT | FOCUS | RMS | | SHIFT | FOCUS | RMS | |
| FRACT | DEG | (MM.) | (MM.) | (WAVES) | STREHL | (MM.) | (MM.) | (WAVES) | STREHL |
| X 0.00 | 0.00 | 0.000000 | 0.000029 | 0.0055 | 0.999 | 0.000000 | −0.000105 | 0.0058 | 0.999 |
| Y 0.00 | 0.00 | 0.000000 | | | | 0.000000 | | | |
| X 0.00 | 0.00 | 0.000000 | 0.000612 | 0.0719 | 0.815 | 0.000000 | −0.000105 | 0.0724 | 0.813 |
| Y 0.43 | 20.00 | −0.000159 | | | | −0.000172 | | | |

TABLE 2B-continued

POLYCHROMATIC WAVEFRONT ANALYSIS OVER VISIBLE SPECTRUM

| | | | | | | | | | |
|---|---|---|---|---|---|---|---|---|---|
| X | 0.00 | 0.00 | 0.000000 | −0.002107 | 0.0716 | 0.817 | 0.000000 | −0.000105 | 0.0741 | 0.802 |
| Y | 0.69 | 30.01 | −0.000033 | | | | 0.000026 | | | |
| X | 0.00 | 0.00 | 0.000000 | 0.000777 | 0.0998 | 0.675 | 0.000000 | −0.000105 | 0.1001 | 0.673 |
| Y | 1.00 | 40.01 | 0.000214 | | | | 0.000213 | | | |

COMPOSITE RMS FOR POSITION 1: 0.06742
Units of RMS are waves at 534.3 nm.
NOTE
Strehl is the intensity at the peak of the point image as a fraction of the peak of the aberration-free image with the same vignetting and obscuration. The approximation used here is generally valid for RMS <0.1.

TABLE 2C

MONOCHROMATIC WAVEFRONT ANALYSIS AT 546.1 nm WAVELENGTH

| | | | | |
|---|---|---|---|---|
| X REL. FIELD | 0.00 | 0.00 | 0.00 | 0.00 |
| Y REL. FIELD | 0.00 | 0.43 | 0.69 | 1.00 |
| WEIGHTS | 1.00 | 1.00 | 1.00 | 1.00 |
| NUMBER OF RAYS | 316 | 280 | 232 | 180 |
| WAVELENGTHS | 643.8 | 546.1 | 480.0 | |
| WEIGHTS | 0 | 1 | 0 | |

| | | | BEST INDIVIDUAL FOCUS | | | | BEST COMPOSITE FOCUS | | |
|---|---|---|---|---|---|---|---|---|---|
| | FIELD | | SHIFT | FOCUS | RMS | | SHIFT | FOCUS | RMS |
| | FRACT | DEG | (MM.) | (MM.) | (WAVES) | STREHL | (MM.) | (MM.) | (WAVES) | STREHL |
| X | 0.00 | 0.00 | 0.000000 | 0.000044 | 0.0020 | 1.000 | 0.000000 | −0.000251 | 0.0045 | 0.999 |
| Y | 0.00 | 0.00 | 0.000000 | | | | 0.000000 | | | |
| X | 0.00 | 0.00 | 0.000000 | 0.000325 | 0.0546 | 0.889 | 0.000000 | −0.000251 | 0.0551 | 0.887 |
| Y | 0.43 | 20.00 | −0.000226 | | | | −0.000236 | | | |
| X | 0.00 | 0.00 | 0.000000 | −0.002382 | 0.0532 | 0.894 | 0.000000 | −0.000251 | 0.0576 | 0.877 |
| Y | 0.69 | 30.00 | −0.000205 | | | | −0.000143 | | | |
| X | 0.00 | 0.00 | 0.000000 | 0.000572 | 0.0451 | 0.923 | 0.000000 | −0.000251 | 0.0457 | 0.921 |
| Y | 1.00 | 40.00 | −0.000306 | | | | −0.000306 | | | |

COMPOSITE RMS FOR POSITION 1: 0.04457
Units of RMS are waves at 546.1 nm.
NOTE
Strehl is the intensity at the peak of the point image as a fraction of the peak of the aberration-free image with the same vignetting and obscuration. The approximation used here is generally valid for RMS <0.1.

TABLE 2D

MONOCHROMATIC WAVEFRONT ANALYSIS AT 1200 nm WAVELENGTH

| | | | | |
|---|---|---|---|---|
| X REL. FIELD | 0.00 | 0.00 | 0.00 | 0.00 |
| Y REL. FIELD | 0.00 | 0.43 | 0.69 | 1.00 |
| WEIGHTS | 1.00 | 1.00 | 1.00 | 1.00 |
| NUMBER OF RAYS | 316 | 280 | 236 | 184 |
| WAVELENGTHS | 1200.0 | | | |
| WEIGHTS | 1 | | | |

| | | | BEST INDIVIDUAL FOCUS | | | | BEST COMPOSITE FOCUS | | |
|---|---|---|---|---|---|---|---|---|---|
| | FIELD | | SHIFT | FOCUS | RMS | | SHIFT | FOCUS | RMS |
| | FRACT | DEG | (MM.) | (MM.) | (WAVES) | STREHL | (MM.) | (MM.) | (WAVES) | STREHL |
| X | 0.00 | 0.00 | 0.000000 | −0.005624 | 0.0104 | 0.996 | 0.000000 | −0.008556 | 0.0209 | 0.983 |
| Y | 0.00 | 0.00 | 0.000000 | | | | 0.000000 | | | |
| X | 0.00 | 0.00 | 0.000000 | −0.009516 | 0.0254 | 0.975 | 0.000000 | −0.008556 | 0.0259 | 0.974 |
| Y | 0.43 | 20.00 | −0.000792 | | | | −0.000777 | | | |
| X | 0.00 | 0.00 | 0.000000 | −0.013188 | 0.0348 | 0.953 | 0.000000 | −0.008556 | 0.0410 | 0.936 |
| Y | 0.69 | 30.00 | −0.001236 | | | | −0.001107 | | | |

TABLE 2D-continued

MONOCHROMATIC WAVEFRONT ANALYSIS AT 1200 nm WAVELENGTH

| X | 0.00 | 0.00 | 0.000000 | −0.009574 | 0.0441 | 0.926 | 0.000000 | −0.008556 | 0.0443 | 0.925 |
|---|------|------|----------|-----------|--------|-------|----------|-----------|--------|-------|
| Y | 1.00 | 40.00 | −0.001320 | | | | −0.001317 | | | |

COMPOSITE RMS FOR POSITION 1: 0.03267
Units of RMS are waves at 1200.0 nm.
NOTE
Strehl is the intensity at the peak of the point image as a fraction of the peak of the aberration-free image with the same vignetting and obscuration. The approximation used here is generally valid for RMS <0.1.

EXAMPLE 2

Tables 2A, 2B, 2C, 2D and FIGS. 4A, 4B, 4C, 4D, 5A, 5B summarize parameters characterizing a related embodiment 400 of the endoscope objective designed for a 1080p high-definition visible and near IR optical sensor with 1.8 micron pixel pitch.

As shown, it is configured in a fashion similar to that of the embodiment 200. Notably, the angular field of view is preserved to be the same in both embodiments 200 and 400. The embodiment 400 of the objective features an effective focal length of 2.37 mm, which means that for a full diagonal field of view of about 80 degrees (and in the absence of significant distortion) it covers a 4 mm diagonal active rectangular area on an optical sensor. The F/number is 2.2, which gives a diffraction-limited Airy disc diameter of about 1.5 microns at a wavelength of 550 nm and twice that (3.0 microns) at a 1100 nm wavelength. This embodiment lends itself for use with a 1080p high-definition visible and near infrared sensor with 1.8 micron pixel pitch. The objective has four mild aspheric surfaces (A1 through A4), shown in red in FIG. 4A. For a stereoscopic system two of these objectives are used in parallel, while the embodiment of the optical detection unit of FIG. 1 includes two optical sensors (126A and another, not shown in FIG. 1). For example, in the case of the two sensors, the optical detection unit includes a first optical sensor configured to received and detect the visible light and a second optical sensor configured to receive and detect the infrared light.

Just like the embodiment 200, the embodiment 400 includes first and second groups of lens elements separated by the stop aperture, and can be used in conjunction with the optical fiber element relaying the image formed by the objective 400 at the image plane I to the corresponding optical sensor 126A. Two optical objectives (each configured according to the embodiment 400) can be used simultaneously, with their optical axes being parallel to one another, and optionally enclosed in the same tubular housing of the endoscope probe) to form a stereoscopic image by delivering light to respectively corresponding optical sensors of the optical detection unit. The system 400 is telecentric in the image space (that is, with respect to the optical sensor).

Figure 4B:
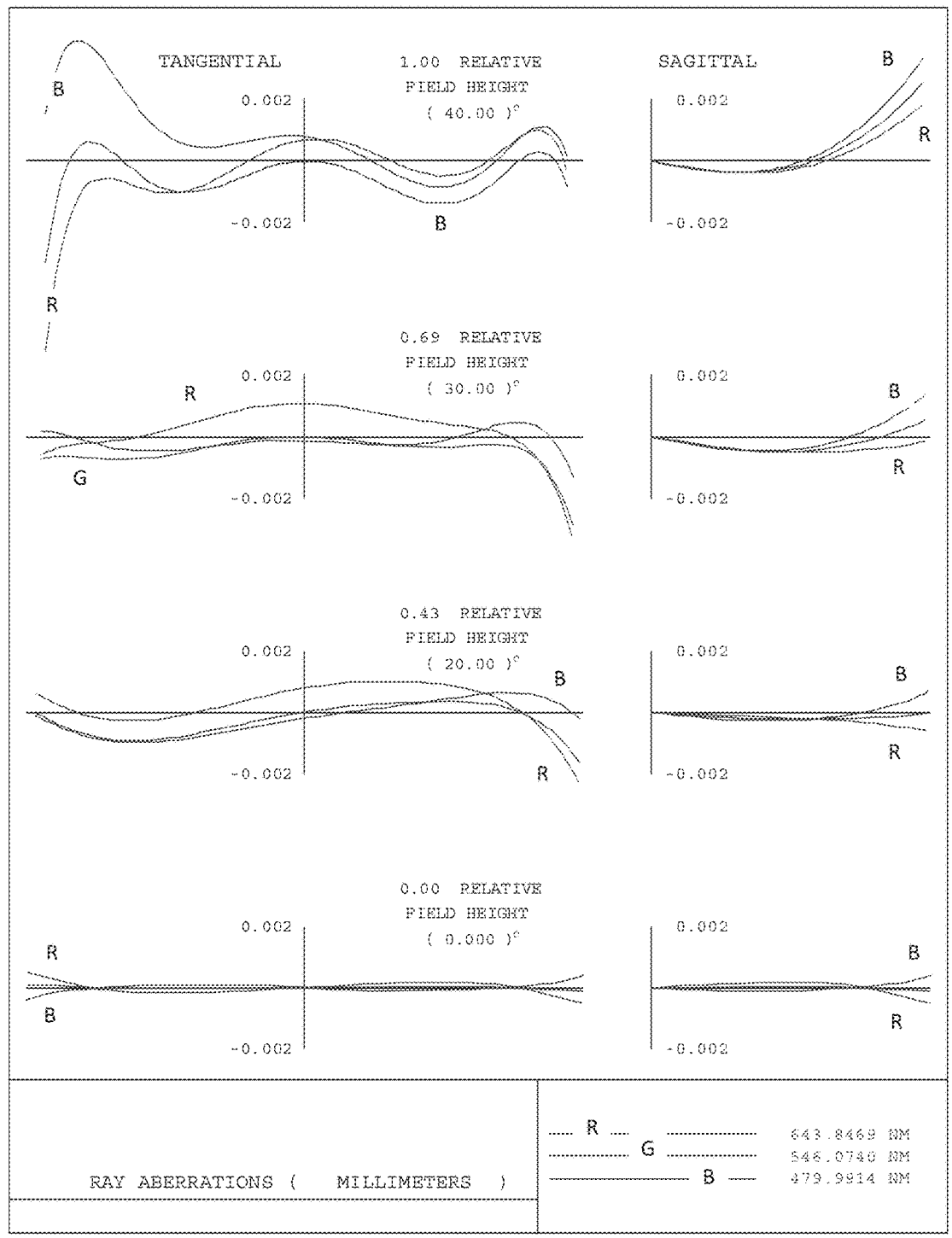
FIG. 4B contains plots illustrating ray aberrations characterizing the design of the embodiment of FIG. 2A.
Figure 4C:
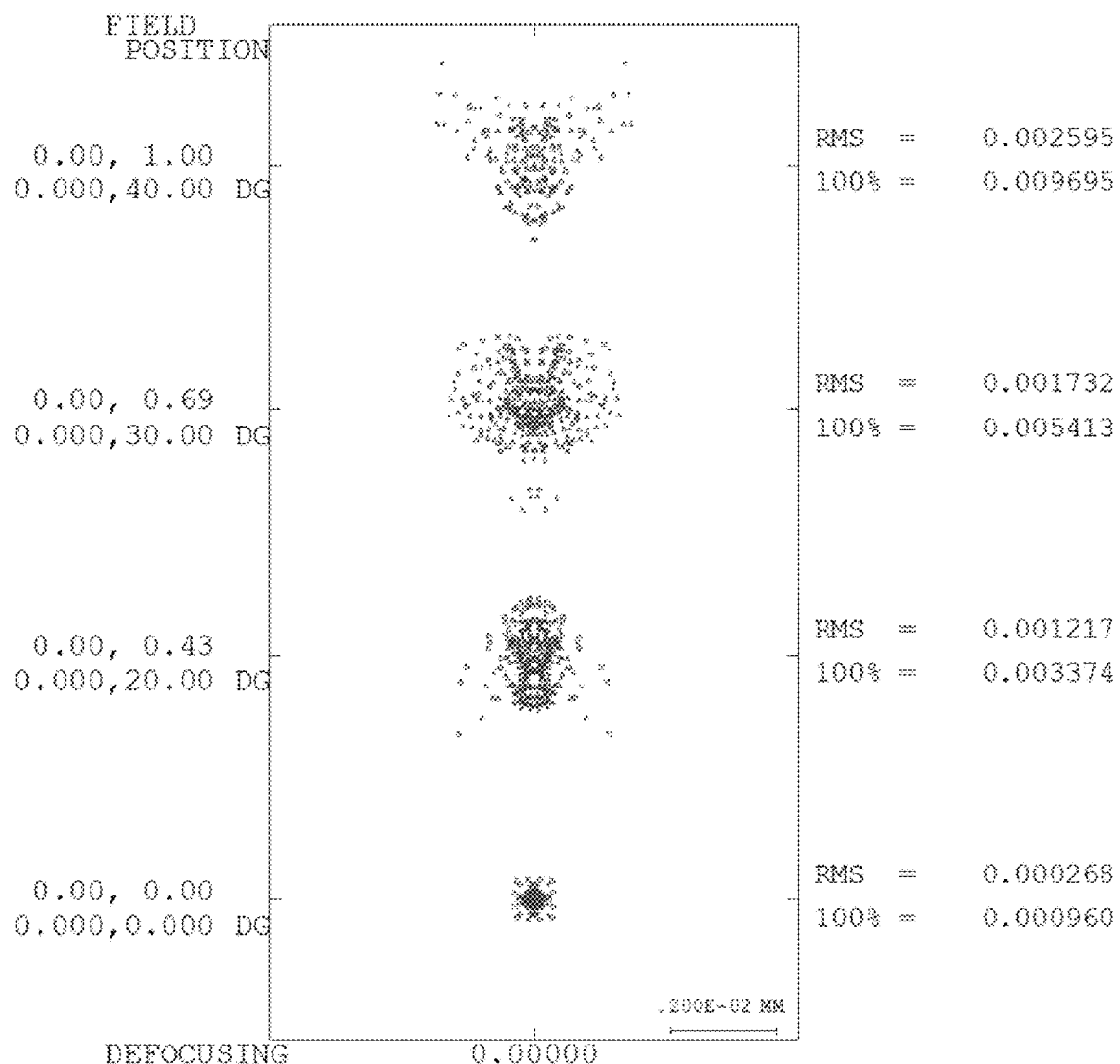
FIG. 4C shows the spot diagrams characterizing imaging at R, G, and B wavelengths with the use of the embodiment of FIG. 4A.
Figure 4D:
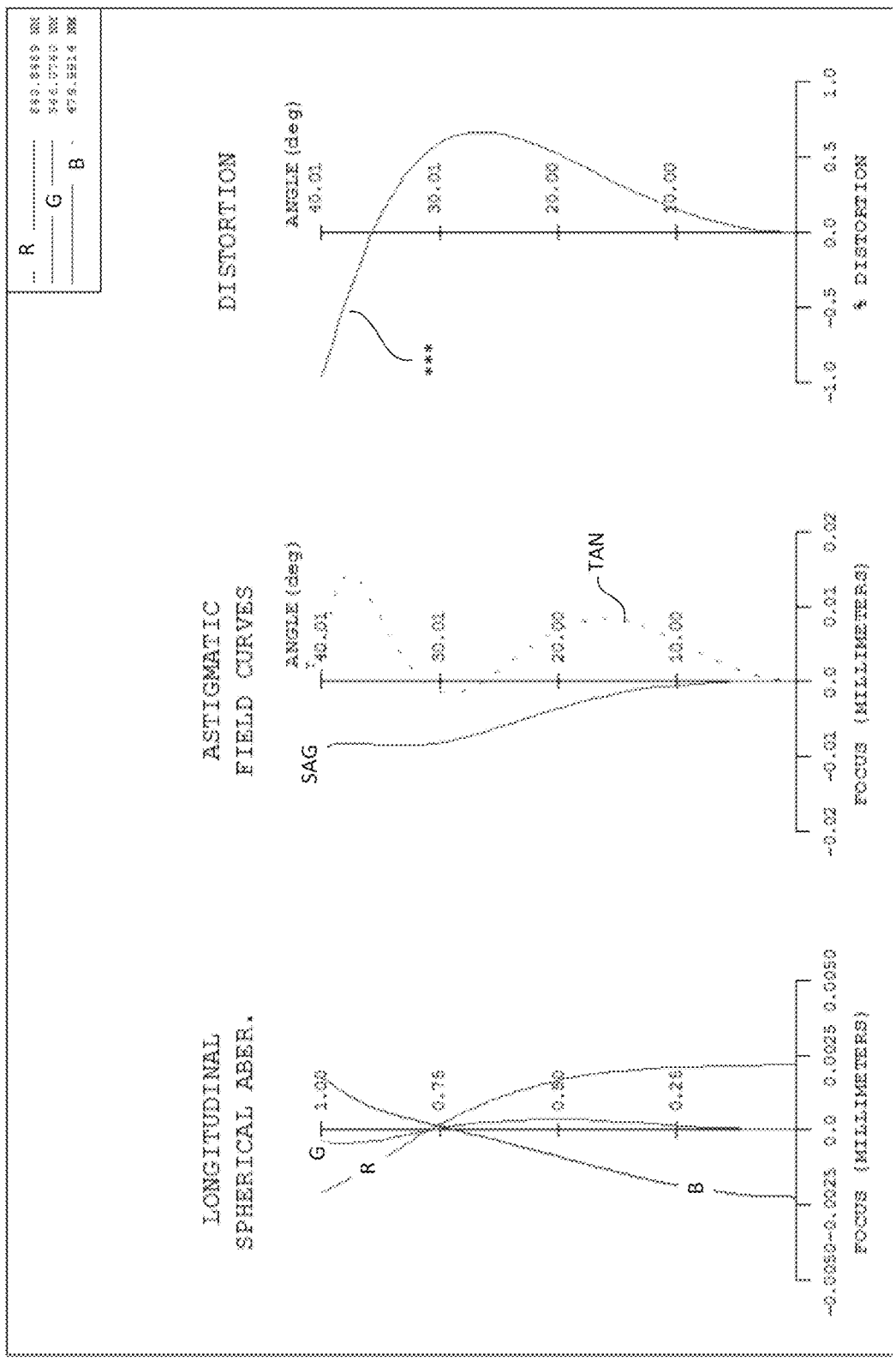
FIG. 4D presents curves representing longitudinal spherical aberration, field curves, and a distortion curve characterizing the imaging properties of the embodiment of FIG. 4A.

FIGS. 4B, 4C illustrate ray aberrations and spot diagrams representing optical performance of the embodiment 400. The distortion figure is notably within 1% for field angles up to 40 degrees (FIG. 4D). Axial color is improved by the use of ED and anomalous glasses (Scott glass, in one specific example). Lateral color aberration(s) over the visible portion of the spectrum remains below 1 pixel.

The analysis of polychromatic performance of the embodiment over the visible portion of the spectrum, Table 2B, evidences that the operation of the objective is reliably characterized by a first Strehl ratio at the central wavelength (546.1 nm) and a second Strehl ratio across the chosen spectral bandwidth (in this example: 480.0 nm . . . 643.8 nm), both of which exceed 0.67 for the fields up to 40 degrees. At the same time, the polychromatic (second) Strehl ratio exceeds 0.81 for any field up to 20 degrees, while still remaining above 0.80 for any field up to 30 degrees. At any value of the field angle up to 40 degrees the ratio of the Strehl ratio at a central wavelength to the Strehl ratio across the chosen visible bandwidth exceeds unity and, in this example, is within the range between about 1.0000 and about 1.0029. The monochromatic analysis of the performance of the embodiment over the visible portion of the spectrum, Table 2C, evidences that the operation of the objective is reliably characterized by the individual Strehl ratio (at the central wavelength chosen to be 546.1 nm) remaining at a value of at least 0.88 for any field up to 40 degrees, and higher than 0.88 for any field up to 30 degrees as well.

At the same time or alternatively, the wavefront analysis in the IR portion of the spectrum (Table 2D) shows that the operation of the embodiment 400 simultaneously exhibits the individual Strehl ratio (at the chosen IR wavelength) exceeding or equal to at least 0.92 for any field angle up to 40 degrees, while remaining above 0.97 for any field angle up to 20 degrees.

FIGS. 5A and 5B illustrate parameters of the modulated transfer function (MTF) characterizing the operation of the embodiment 400 in the visible portion of the spectrum and in light at 1200 nm. A skilled artisan would appreciate that quality of an image at the plane I is diffraction-limited in the vicinity of the optical axis.

Figure 6:
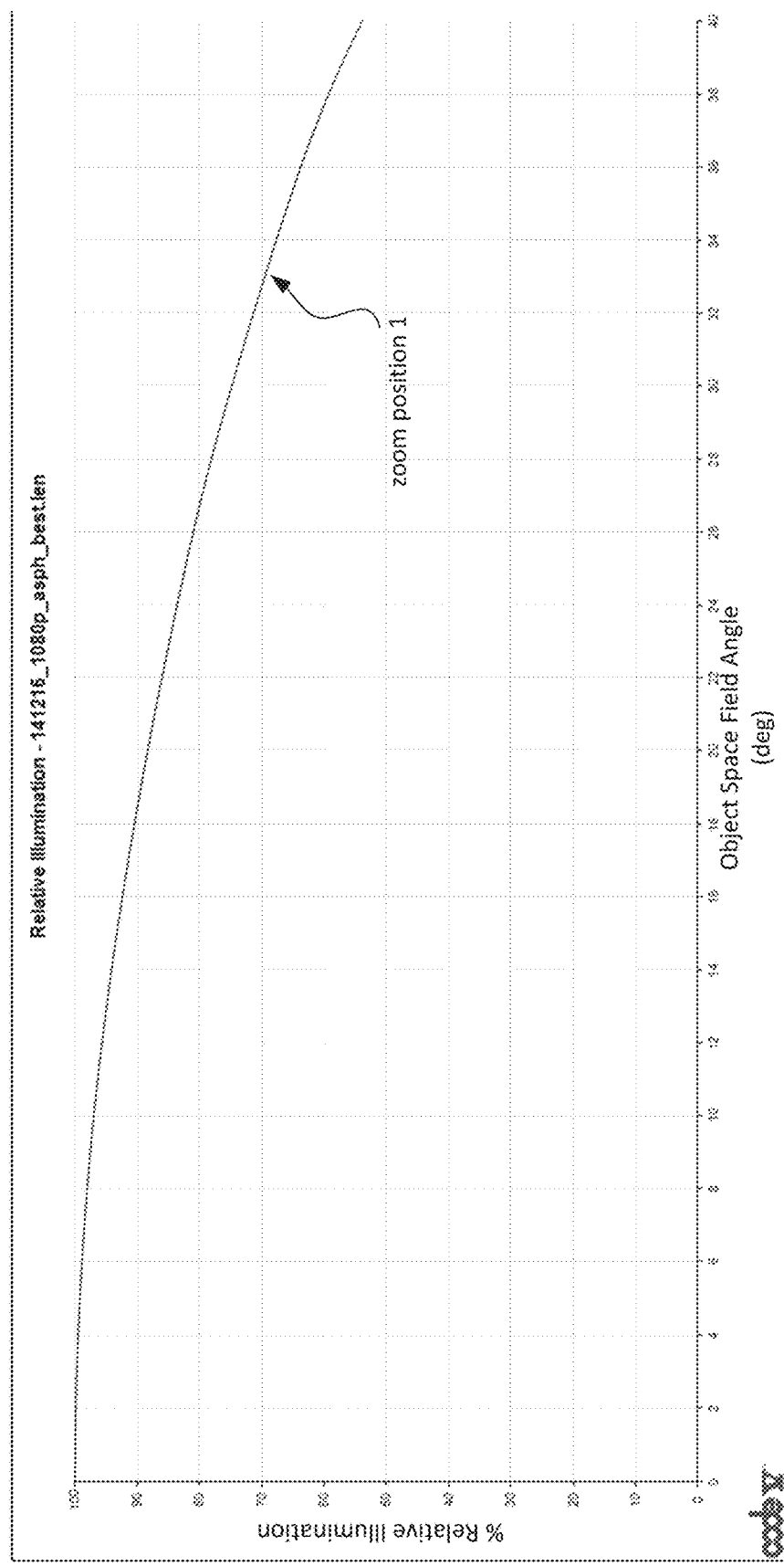
FIG. 6 is a plot representing relative illumination as a function of the object space field angle.

The plot of FIG. 6, represents relative illumination in the system with about 50% at the end of the field (which value can be varied with the use of applicable program code).

The related idea of the present invention stems from the realization that optical data, acquired with the use of a multispectral stereoscopic endoscope system (such as one of those described above) may be used in parallel to ensure stereoscopic imaging and increase depth of field, resolution or spectral content in one of the following general ways described below.

EXAMPLE 3

Two substantially identical objectives are configured to image a scene in the visible spectral band onto two sensors of 720p or higher pixel count with 1.5 micron pixels. The first optical sensor is set to either a near or far focal point, and the second sensor has the focal point at the opposite location from the first sensor such that a larger focal range can be created by fusing the resulting images formed based on data received, respectively, from the first and second objectives. The best focus is chosen by using the image closest to the desired focal position as the primary image. The composite focused image may be created with the use of electronic circuitry that includes data-processing unit by starting at the most clearly focused area of the primary sensor, and working outward. When an area of the secondary sensor is more clearly in focus, that optical information captured by the secondary sensor is used, resulting in a composite image that combines the best portions of images formed based on data received from the two available optical channels. An additional, third objective can be employed to procure image data at longer-wavelength light (for example, in the near-infrared band) onto a corresponding sensor sensitive to infrared light. Such sensor may have larger pixels such as 2.8 micron in size, which matches the larger diffraction-limited Airy disc and improves signal-to-noise. Visible stereo stream of optical data from the first two channels may be filtered through Bayer filters, but the third channel may have no filter, or, alternatively, a custom filter design for the near infrared. Imagery from the larger pixeled infrared sensor will be processed to properly register with the visible imagery.

Figure 7A:
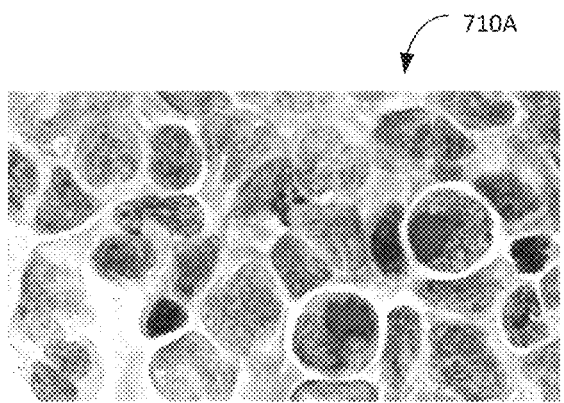
FIGS. 7A, 7B provide simulated left and right images from an endoscope (i.e., images acquired with an endoscope's left and right objectives in a visible portion of the spectrum) with two overlapping fields of view. In a specific implementation, the right image may represent the visible image acquired by the sensor with sensitivity extended into the near infrared.
Figure 7B:
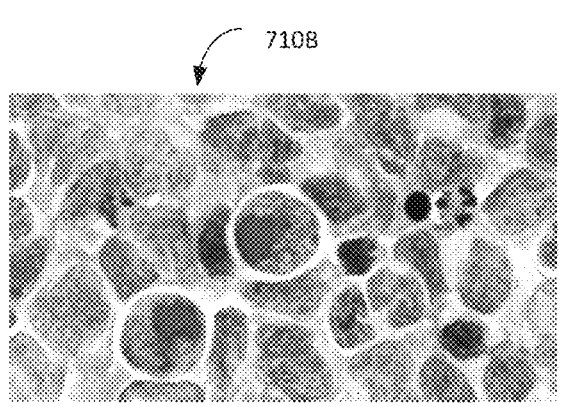
Figure 8:
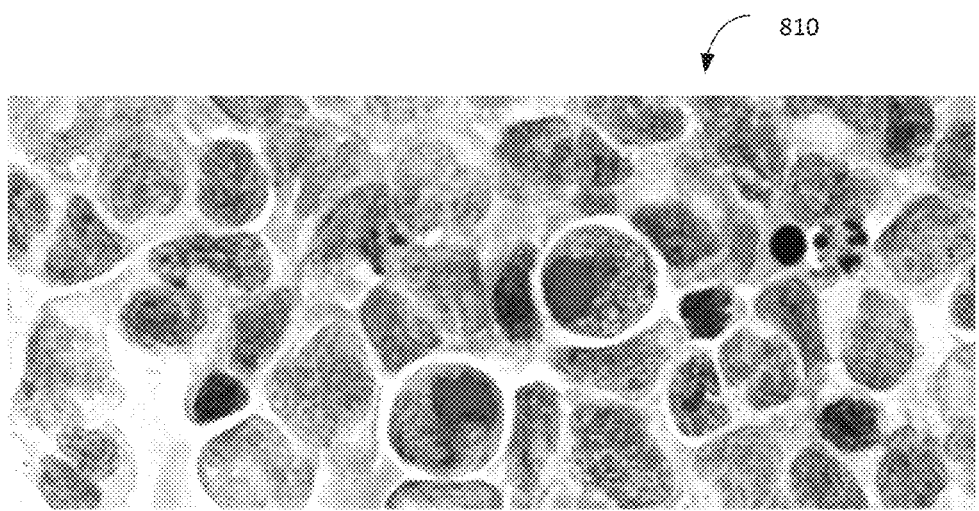
FIG. 8 shows a composite image formed by a combination of the left and right images of FIGS. 7A, 7B.
Figure 9:
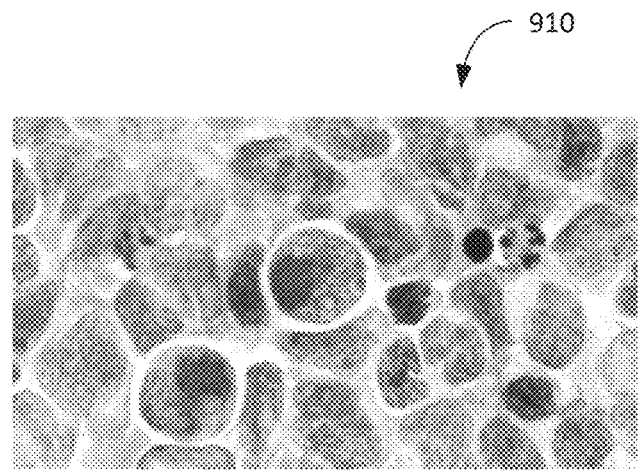
FIG. 9 shows the image of the scene acquired in the NIR portion of the spectrum with an embodiment of the invention.
Figure 10:
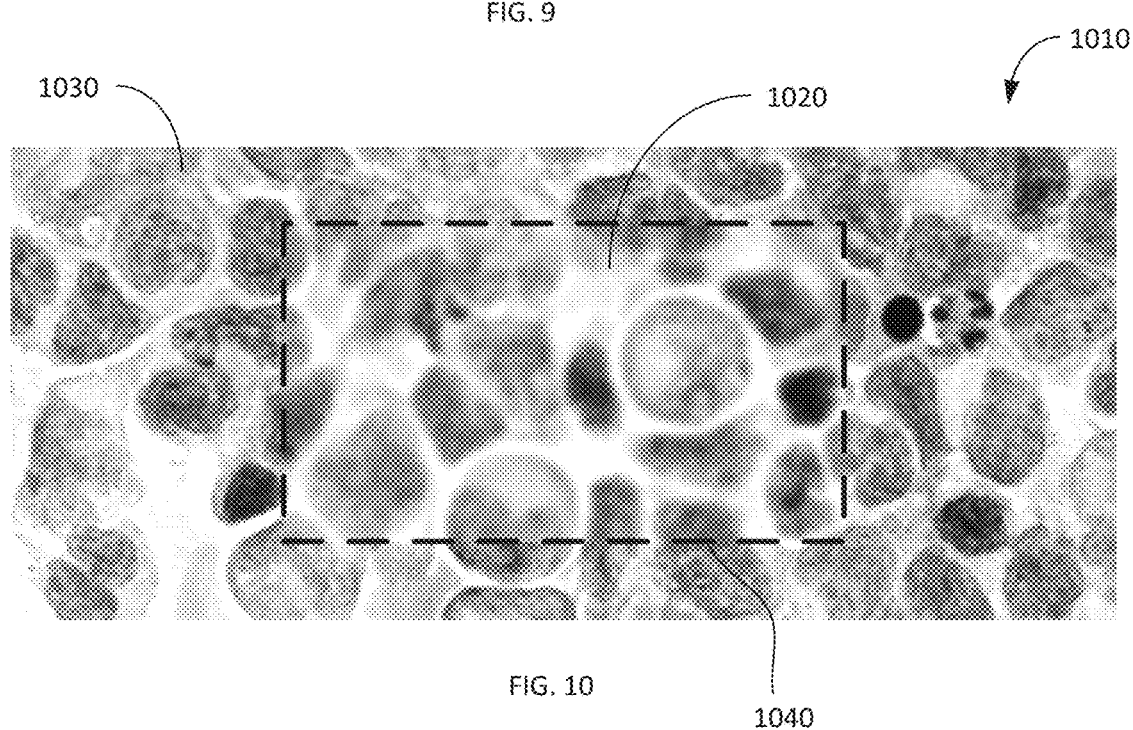
FIG. 10 is a fused image containing portions of images of FIGS. 8 and 9. Here, an IR overlay, and image fusion to provide a focused image, result in a composite image with both image processing steps included.

Here, constituent images acquired from the different fields of view with the use of multiple objectives of the endoscopic system are combined into a single composite image. For example, the two visible channel images 710A, 710B, shown in FIGS. 7A, 7B respectively, are combined to produce the composite image 810 of FIG. 8. The image 810 is later fused with at least a portion of the disparate image 910 of the scene acquired in the near-IR portion of the spectrum, FIG. 9, into a single image 1010 of FIG. 10 for further use (in one example—for diagnostic purposes). As shown in FIG. 10, a portion 1020 of the NIR image 910, appropriately scaled, is embedded into or alternatively, spatially combined with the composite image 810 of FIG. 8 resulting in a fused image 1010 in which a portion 1030 representing the embedding or combining part of the image 810 is stitched or merged with the portion 91020 being embedded or combined along a spatial boundary shown as 1040.

EXAMPLE 4

An endoscope with two identical objectives is used to image the scene in the visible spectral band onto two optical sensors of 720p or higher pixel count. One sensor may have, for example, 1.5 micron-sized pixels and be equipped with a Bayer color filter, or custom filter arrangement. A second sensor that is additionally sensitive in the near and mid-infrared spectral bands has 2.8 micron pixels (or smaller) while having no Bayer filter to filter out light incident onto the second sensor. Alternatively or in addition, a custom color filter may be used to enhance a portion, or all of the second sensor imagery. Images formed with the use of the second sensor are registered and fused to those formed with the use of the first sensor. The optical system employing the objective(s) at hand is configured such that the first sensor is optically-conjugate to either a near- or far object distance, while the second sensor will have the operational point at the location opposite from the first sensor such that a larger focal range can be created by fusing the images acquired with the first and second sensors. The best focus is chosen by using the image closest to the desired focal position as the primary image. The composite focused image is created by starting at the most clearly focused object area of the primary sensor, and working outward. When an area of the secondary sensor is more clearly in focus, that information will be used, resulting in a composite image that uses the best portions from the two available optical channels.

In so procuring the constituent images, Illumination of the object may be provided by a light source with multiple individually controllable light-emitting units, to eliminate a need to distinguish between different spectral bands. The light source can be driven to multiplex the different spectral bands temporally with sufficient speed to not hinder video refresh rates. Eliminating all filters as well as those directly on the sensor also removes the need for demosaicing that would be required when using a Bayer filter.

A skilled person would readily appreciate that the multiple objective lenses of an embodiment of the endoscope system should be of low distortion and well corrected at multiple focal points. Image processing to fuse the two channels of information enhances the base color image given in the first channel. By incorporating the infrared imagery from the second channel, additional information across a large spectral band can be presented in the final image.

Embodiments of the multi-lens embodiments of an endoscope system are configured to provide for multi-spectral stereoscopic imaging of object(s) or targets located at different object distances (from a reference plane in the optical system, as known in the art) with a fixed field-of-view and without movable parts (no "zooming" involved). An embodiment utilizes:—two simultaneously acquired images of the same target (three images may be optionally used, as suggested above), among which an image of a first portion of the target located at a first distance closer to the reference plane ("closer image") is acquired through the first optical channel, and an image of a second portion of the target located at a second distance farther from the reference plane ("farther image"), possibly in a different spectral window, is acquired through another optical channel. Based on the "image fusion" image-processing methodology of related art, the optical data is then formed from which, according to an idea of the invention, a high spatial-resolution image of a portion of a target at any distance between the first and second distance is then derived.

The application of such embodiments finds its use in the field of laparoscopic imaging with different markers/dyes, which have affinity to particular types of tissue, that requires both visible (VIS) and near-IR (NIR) optical channels. Different optical channels use different optical sensors (CCDs, InGaAs, etc. such as those discussed, for example, in U.S. patent application Ser. No. 15/099,346 the disclosure of which is incorporated herein by reference) and, while having equal focal lengths, are configured to image the target using different fixed focal positions.

It is appreciated that some of the steps of the embodiments of the method of the invention can be effectuated with a processor controlled by instructions stored in a tangible, non-transitory storage memory. The memory may be random access memory (RAM), read-only memory (ROM), flash memory or any other memory, or combination thereof, suitable for storing control software or other instructions and data. Some of the functions performed by the processor have been described with reference to flowcharts and/or block diagrams. Those skilled in the art should readily appreciate that functions, operations, decisions, etc. of all or a portion of each block, or a combination of blocks, of the flowcharts or block diagrams may be implemented as computer program instructions, software, hardware, firmware or combinations thereof. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

References made throughout this specification to "one embodiment," "an embodiment," "a related embodiment," or similar language mean that a particular feature, structure, or characteristic described in connection with the referred to "embodiment" is included in at least one embodiment of the present invention. Thus, appearances of these phrases and terms may, but do not necessarily, refer to the same implementation. It is to be understood that no portion of disclosure, taken on its own and in possible connection with a figure, is intended to provide a complete description of all features of the invention.

It is also to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed.

The invention as recited in claims appended to this disclosure is intended to be assessed in light of the disclosure as a whole, including features disclosed in prior art to which reference is made.

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

The invention claimed is:

1. A method for forming an image, the method comprising:
    transmitting light through a first group of lens elements of a first optical objective of an endoscope probe, disposed within a housing of the endoscope probe, onto an aperture stop located immediately adjacently to and after the first group of lenses, wherein said transmitting light through the first group of lens elements includes transmitting light through a first meniscus lens element and then transmitting light through a first optical doublet; and
    transmitting light from the aperture stop through a second group of lens elements of said first optical objective of the endoscope probe to form a first image in an image plane, the second group including a sequence of second, third, and fourth optical doublets,
    wherein the transmitting light through the second group of lens elements includes transmitting light through a second meniscus lens that has a positive dioptric power and that is positioned between said sequence of optical doublets and the image plane, and
    wherein each one of the transmitting light through the first group of lens elements and transmitting light through the second groups of lens elements includes transmitting light through two aspheric refractive surfaces.

2. A method according to claim 1, wherein the transmitting light through the first group of lens elements includes transmitting light through the first meniscus lens having a negative dioptric power.

3. A method according to claim 1, further comprising transmitting light from the image plane through an optical fiber element towards a first optical sensor.

4. A method according to claim 1, further comprising receiving light from said first image with an optical sensor positioned, within said housing, at the image plane.

5. A method according to claim 1, further comprising transmitting light through a second optical objective of the endoscope probe disposed within said housing to form a second image at the second plane, said second optical objective having an axis parallel to an axis of the first objective.

6. A method according to claim 1, wherein the first objective is telecentric in image space.

7. A method according to claim 1, comprising receiving light transmitted through the first optical objective of the endoscope probe at a first optical detector, and further comprising:
    receiving light transmitted through a second optical objective of the endoscope probe at a second optical detector, the first optical objective and the second optical objective having respective first and second field-of-views (FOVs), and
    with the use of a programmable computer processor, fusing first and second optical data received by said processor from the first and second optical detectors, respectively, to form a composite image in which a first portion of said image represents the first optical data and a second portion of said image represents the second optical data.

8. A method according to claim 7, wherein said receiving light at the first optical detector includes receiving light within a first spectral window and said receiving light at the second optical detector includes receiving light within a second spectral window, said first and second spectral windows being different from one another.

9. A method according to claim 7, further comprising:
    positioning the first optical detector to be optically-conjugate, through the first optical objective, to a first point; and
    positioning the second optical detector to be optically-conjugate, through the second optical objective, to a second point,
    the first and second points being at different object distances from respectively-corresponding first and second optical objectives such that a focal range represented in the composite image is greater than any of focal ranges of the first and second optical objectives, respectively.

10. An endoscope probe system comprising:
a tubular housing; and
a first optical objective of the endoscope probe system inside said tubular housing, the first optical objective including first and second groups of lens elements, wherein
  the first group of lens elements includes
    a) a first meniscus lens with a negative dioptric power, and
    b) a first optical doublet; and
  the second group of lens elements includes a sequence of second, third, and fourth optical doublets and a second meniscus lens;
  wherein at least one of the first and second groups of lens elements includes an aspheric refractive surface;
  wherein the first optical doublet is disposed between the first meniscus lens and the second group of lens elements, and
  wherein an aperture stop is defined between the first and second optical doublets;
wherein the first optical objective exhibits distortion below 1% for field angles up to at least 40 degrees while, at the same time, having a ratio of first and second Strehl ratios that exceeds unity for any field angle up to 40 degrees,
wherein each of the first and second Strehl ratios is above 0.92 for any field angle up to 20 degrees,
wherein a polychromatic operation of said first objective is characterized by both the first Strehl ratio and the second Strehl ratio exceeding 0.844 for any field angle up to 40 degrees, and
wherein the first Strehl ratio is defined at a central wavelength of a predefined bandwidth of a visible spectrum, wherein the second Strehl ratio is defined across said predefined bandwidth of the visible spectrum.

11. An endoscope probe system according to claim 10, further comprising an optical fiber element disposed inside the tubular housing to collect light that has propagated through the first optical objective.

12. An endoscope probe system according to claim 10, wherein the first optical objective is telecentric in image space.

13. An endoscope probe system according to claim 10, wherein monochromatic operation of said first objective is characterized by both first and third Strehl ratios being no less than 0.970 at any field angle up to 40 degrees, wherein the third Strehl ratio is defined at a chosen infrared (IR) wavelength.

14. An endoscope probe system according to claim 10, wherein the first optical objective has a first field of view (FOV), and further comprising:
a second optical objective of the endoscope probe system, the second optical objective having a second FOV, said first and second optical objectives optically accommodated to form a respectively-corresponding image at respectively-corresponding first and second optical detectors associated with the endoscope probe; and
a programmable processor configured to receive, respectively, first and second optical data from the first and second optical detectors and to form a composite image in which a first portion of said image representing the first optical data is fused with a second portion of said image representing the second optical data.

15. An endoscope probe system according to claim 14, wherein a first combination of the first optical objective and the first optical detector and a second combination of the second optical objective with the second optical detector are configured to form, respectively, said first and second optical data carrying information in first and second spectral windows.

16. An endoscope probe system according to claim 15, wherein the first and second spectral windows do not overlap.

17. An endoscope probe system according to claim 15, wherein the first and second FOVs differ from one another.

18. An endoscope probe system according to claim 14, wherein the first optical detector is positioned to be optically-conjugate to a first point defined at a first object distance from the first optical objective, while the second optical detector is positioned to be optically-conjugate to a second point defined at a location opposite from the first point sensor such that the composite image represents a scene within a focal range that is larger than any of the first and second focal ranges, the first and second focal ranges respectively associated with the first and second optical objectives.

19. A method according to claim 1, wherein the transmitting light from the aperture stop through the second group of lens elements includes transmitting said light through the sequence of the second, third, and fourth optical doublets each of which has a corresponding positive optical power.

20. An endoscope system according to claim 10, wherein each of the second, third, and fourth optical doublets has a positive optical power.

21. An endoscope system according to claim 10, wherein the second meniscus lens of the second group of lens elements is a lens element immediately adjacent to an image plane of the endoscope system.

22. An endoscope system according to claim 10, wherein each of the first and second groups of lenses includes two aspheric refractive surfaces.

23. An endoscope probe system comprising:
a tubular housing; and
a first optical objective of the endoscope probe system inside said housing, the first optical objective including first and second groups of lens elements, wherein
  the first group of lens elements includes
  a) a first meniscus lens with a negative dioptric power, and
  b) a first optical doublet; and
    the second group of lens elements includes a sequence of second, third, and fourth optical doublets and a second meniscus lens, wherein the second meniscus lens has a positive dioptric power an is positioned between the sequence and an image plane;
  wherein the first optical doublet is disposed between the first meniscus lens and the second group of lens elements, and
  wherein an aperture stop is defined between the first and second optical doublets, and
  wherein each of the first and second groups of lens elements includes two aspheric refractive surfaces.

24. An endoscope probe system according to claim 23, wherein the first optical objective is telecentric in image space.

* * * * *